US012056280B2

(12) United States Patent
Tadi et al.

(10) Patent No.: US 12,056,280 B2
(45) Date of Patent: Aug. 6, 2024

(54) BRAIN ACTIVITY MEASUREMENT AND FEEDBACK SYSTEM

(71) Applicant: MINDMAZE GROUP SA, Lausanne (CH)

(72) Inventors: Tej Tadi, Lausanne (CH); Gangadhar Garipelli, Lausanne (CH); Daniel Perez Marcos, Lausanne (CH); Nicolas Bourdaud, Paris (FR); Gerardo De Jesus Chavez Castaneda, Fraccionamiento Tabachines (MX); Leandre Bolomey, Prevonloup (CH)

(73) Assignee: MINDMAZE GROUP SA, Lausanne (CH)

( * ) Notice: Subject to any disclaimer, the term of this patent is extended or adjusted under 35 U.S.C. 154(b) by 342 days.

(21) Appl. No.: 17/000,872

(22) Filed: Aug. 24, 2020

(65) Prior Publication Data

US 2021/0208680 A1 Jul. 8, 2021

Related U.S. Application Data

(63) Continuation of application No. 15/555,561, filed as application No. PCT/IB2016/051125 on Mar. 1, 2016, now abandoned.

(30) Foreign Application Priority Data

Mar. 2, 2015 (EP) .................................... 15157206

(51) Int. Cl.
*A61B 5/1455* (2006.01)
*A61B 5/00* (2006.01)
(Continued)

(52) U.S. Cl.
CPC ............ *G06F 3/015* (2013.01); *A61B 5/0036* (2018.08); *A61B 5/291* (2021.01); *A61B 5/375* (2021.01);
(Continued)

(58) Field of Classification Search
CPC ........ A61B 5/1455; A61B 5/6814; A61B 5/01
See application file for complete search history.

(56) References Cited

U.S. PATENT DOCUMENTS 6,301,493 B1 10/2001 Marro
2002/0128541 A1 9/2002 Kim
(Continued)

FOREIGN PATENT DOCUMENTS

EP 0541393 5/1993
WO 2011038103 3/2011

*Primary Examiner* — Marjan Fardanesh
(74) *Attorney, Agent, or Firm* — GRAESER ASSOCIATES INTERNATIONAL INC; Dvorah Graeser

(57) ABSTRACT

A head set (2) comprises a brain electrical activity (EEG) sensing device (3) comprising EEG sensors (22) configured to be mounted on a head of a wearer so as to position the EEG sensors (22) at selected positions of interest over the wearers scalp, the EEG sensing device comprising a sensor support (4) and a flexible circuit (6) assembled to the sensor support. The sensor support and flexible circuit comprise a central stem (4a, 6a) configured to extend along a center plane of the top of the head in a direction from a nose to a centre of the back of a wearers head, a front lateral branch (4b, 6b) configured to extend across a front portion of a wearer's head extending laterally from the central stem, a center lateral branch (4c, 6c) configured to extend across a top portion of a wearer's head essentially between the wearer's ears, and a rear lateral branch (4d, 6d) configured to extend across a back portion of a wearer's head. The sensor support (4) comprises a base wall (401) and side walls (402) extending along edges of the base wall to form an essentially flat "U" shaped channel (403) in which the flexible circuit (6) is inserted and the base wall comprise EEG sensor orifices (404) to allow access to the EEG sensor contacts or electrodes on the flexible circuit.

20 Claims, 24 Drawing Sheets

(51) Int. Cl.
  *A61B 5/291* (2021.01)
  *A61B 5/375* (2021.01)
  *G02B 27/01* (2006.01)
  *G06F 3/01* (2006.01)
  *H01L 33/58* (2010.01)
  *A61B 5/01* (2006.01)
  *A61B 5/0533* (2021.01)
  *A61B 5/11* (2006.01)
  *A61B 5/30* (2021.01)
  *A61B 5/318* (2021.01)
  *A61B 5/389* (2021.01)
  *A61B 5/398* (2021.01)

(52) U.S. Cl.
  CPC .......... *A61B 5/6814* (2013.01); *G02B 27/017* (2013.01); *G02B 27/0172* (2013.01); *G06F 3/012* (2013.01); *G06F 3/013* (2013.01); *H01L 33/58* (2013.01); *A61B 5/01* (2013.01); *A61B 5/0533* (2013.01); *A61B 5/1114* (2013.01); *A61B 5/1128* (2013.01); *A61B 5/30* (2021.01); *A61B 5/318* (2021.01); *A61B 5/389* (2021.01); *A61B 5/398* (2021.01); *A61B 5/4836* (2013.01); *A61B 5/486* (2013.01); *A61B 5/6831* (2013.01); *A61B 5/7285* (2013.01); *A61B 5/743* (2013.01); *A61B 5/744* (2013.01); *A61B 5/7445* (2013.01); *A61B 2562/164* (2013.01); *A61B 2562/166* (2013.01)

(56) References Cited

U.S. PATENT DOCUMENTS

| | | |
|---|---|---|
| 2008/0306397 A1 | 12/2008 | Bonmassar |
| 2011/0282231 A1 | 11/2011 | Pradeep |
| 2013/0172721 A1 | 7/2013 | McPeck |
| 2015/0011857 A1* | 1/2015 | Henson ................ A61B 5/6831 600/383 |
| 2015/0282760 A1 | 10/2015 | Badower |

* cited by examiner

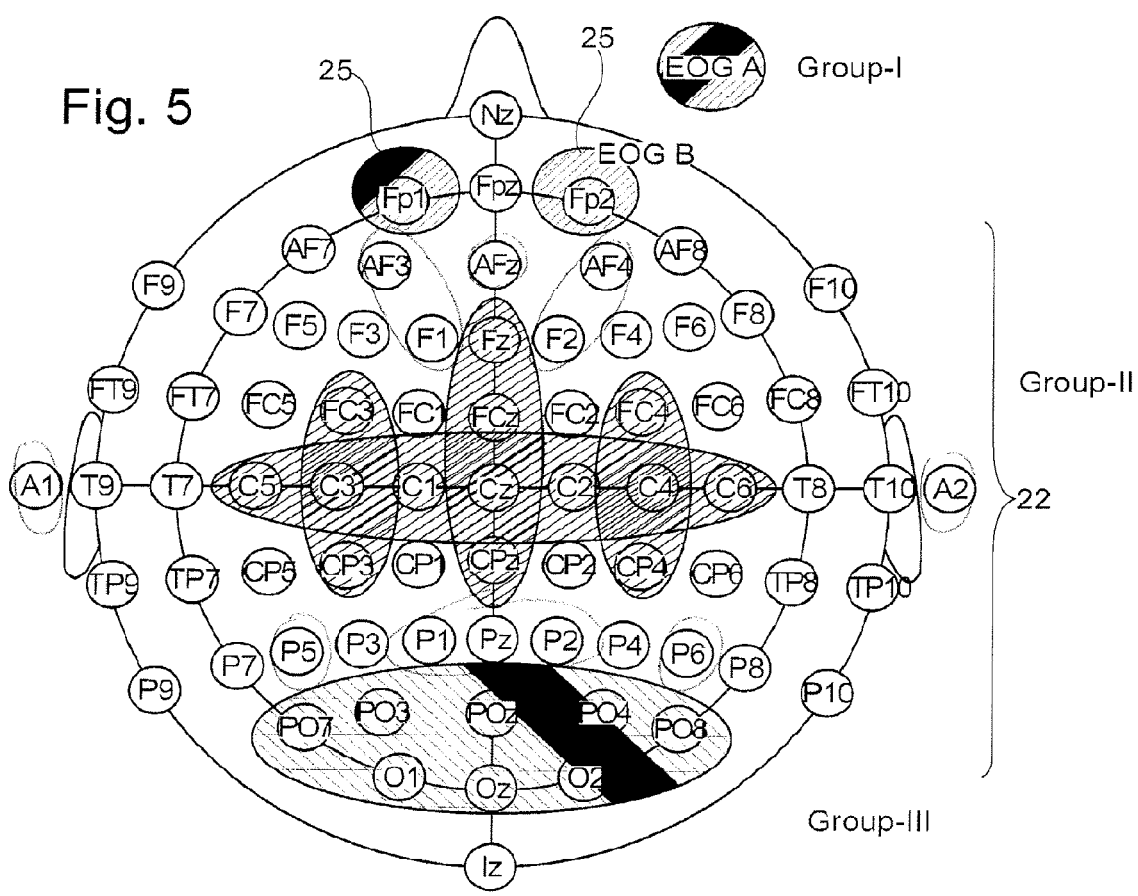

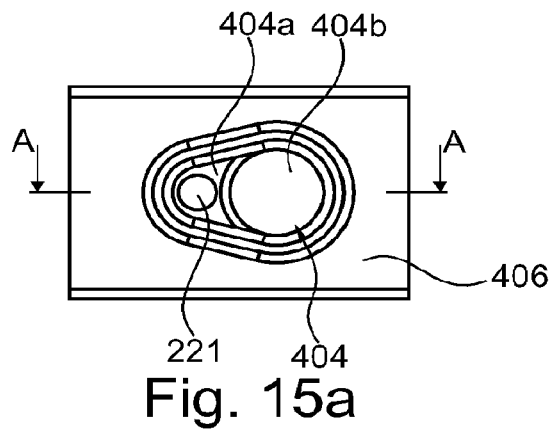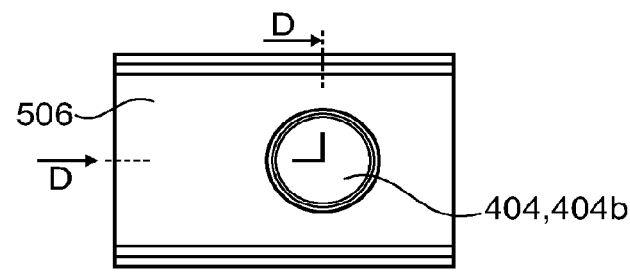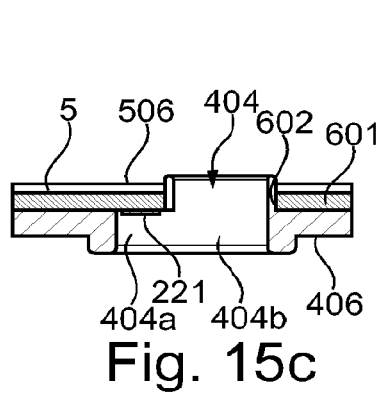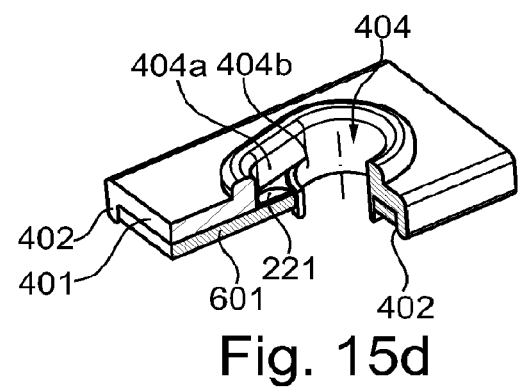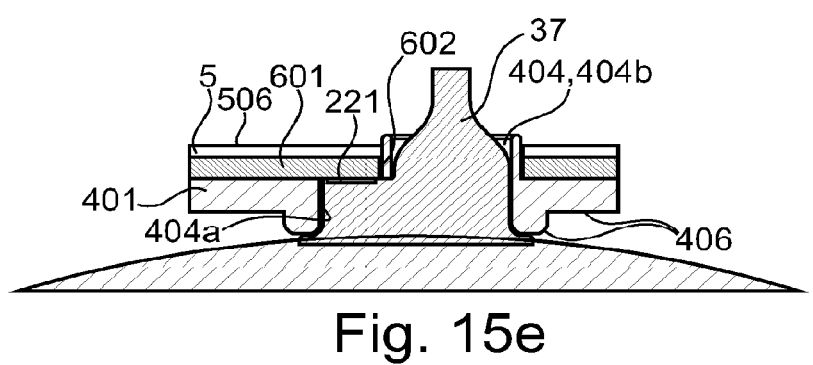

BRAIN ACTIVITY MEASUREMENT AND FEEDBACK SYSTEM

TECHNICAL FIELD

The present invention relates to a head-mounted device to measure or monitor cortical activity of a user, and optionally to generate stimuli and/or to provide feedback to the user. Applications for use of the invention may include gaming, training, learning of sensory-motor skills, diagnosis or treatment of neurological injury or disease.

DESCRIPTION OF RELATED ART

Neurological injury which follows a stroke often manifests as hemiparesis or other partial paralysis of the body. Current rehabilitation procedures are often based on exercises performed by the impaired body part, the movement of which is tracked in real-time to provide feedback to the patient and/or a medical practitioner. Computer controlled mechanical actuation systems have been used to track a position of, and force applied by, a body part such an arm of a patient as a predetermined movement pattern is executed by the patient. To reduce patient fatigue such systems can support the patient, for example by actuators which can assist during execution of the movement. A disadvantage of such devices is that they can be complicated and expensive. Also, conventional systems are based on tracking actual movements and are therefore not adapted for diagnosis or treatment in the very early stages after an occurrence of stroke where movement is impaired or very limited. They may also present a risk to the patent if, for example, the body part is moved too quickly or if part of the heavy actuation equipment falls on the patent. They are also not particularly portable, which generally prohibits home use and use in a hospital environment, and can also be difficult to adapt to the rehabilitation requirements of a particular patient since the range of permitted movements is often confined by a mechanical system.

US 2011/0054870 discloses a VR based system for rehabilitation of a patient, wherein a position of a body part of a patient is tracked by a motion camera. Software is used to create a motion avatar, which is displayed to the patient on a monitor. In an example, if a patient moves only a right arm when movement of both arms are prescribed, then the avatar can also display motion of the left arm.

A similar system is disclosed in 'The design of a real-time, multimodal biofeedback system for stroke patient rehabilitation', Chen, Y et al., ACM International Conference on Multimedia, 23 Oct. 2006, wherein infra-red cameras are used to track a 3-dimensional position of markers on an arm of a patient. Using a monitor, in VR a position of the arm of the patient is displayed as predefined movement patterns are completed, such as the grasping of a displayed image.

A drawback of certain VR based systems is that they only measure the response of the body part to an instructed task. Accordingly, they do not directly measure cortical activity in response to a displayed movement of a body part, only the way in which an area of the brain can control a body part. This may lead to areas of the brain being treated other than those which are damaged, or at least an inability to directly monitors a particular area of the brain. Moreover, the patient is not fully immersed in the VR environment since they look to a separate monitor screen to view the VR environment.

In WO 2011/123059 and US 2013/046206, VR based systems with brain monitoring and motion tracking are described, the main drawback of known systems being that they do not reliably nor accurately control synchronization between stimulation or action signals and brain activity signals, which may lead to incorrect or inaccurate processing and read out of brain response signals as a function of stimuli or actions.

In conventional systems, in order to synchronize multi-modal data (including physiological, behavioral, environmental, multimedia and haptic, among others) with stimulation sources (e.g., display, audio, electrical or magnetic stimulation) several independent, dedicated (i.e. for each data source) units are connected in a decentralized fashion, meaning that each unit brings its inherent properties (module latencies and jitters) into the system. Additionally, these units may have different clocks, therefore acquiring heterogenous data with different formats and at different speeds. In particular, there is no comprehensive system that comprises stereoscopic display of virtual and/or augmented reality information, where some content may be related to some extent to the physiological/behavioral activity of any related user and registered by the system, and/or any information coming from the environment. Not fulfilling the above-mentioned requirements may have negative consequences in various cases in different application fields, as briefly mentioned in the following non-exhaustive list of examples:

a) Analysis of neural responses to stimulus presentation is of importance in many applied neuro-science fields. Current solutions compromise the synchronization quality, especially in the amount of jitter between the measured neural signal (e.g., EEG) and the simulation signal (e.g., display of a cue). Due to this, not only the signal to noise ratio of acquired signals is lowered but also limit the analysis to lower frequencies (typically less than 30 Hz). A better synchronization ensuring least jitter would open up new possibilities of neural signals exploration in the higher frequencies as well as precise (sub millisecond) timing based stimulation (not only non-invasive stimulation, but also invasive stimulation directly at the neural cite and subcutaneous stimulation).

b) Virtual reality and body perception: If the synchronization between the capture of user's movements and their mapping onto a virtual character (avatar) that reproduces the movement in real time is not achieved, then, the delayed visual feedback of the performed movement via a screen or head-mounted display will give to the user the feeling that he/she is not the author of such movement. This may have important consequences in motor rehabilitation, where patients are trained to recover mobility, as well as for training or execution of extremely dangerous operation as deactivating a bomb by manipulating a robot remotely.

c) Brain-computer interfaces: If the synchronization between motor intention (as registered by electroencephalographic data), muscle activity and the output towards a brain body-controlled neuroprosthesis fails, it is not possible to link motor actions with neural activation, preventing knowledge about the neural mechanisms underlying motor actions necessary to successfully control the neuroprosthesis.

d) Neurological examinations: The spectrum of electroencephalographic (EEG) data may reach up to 100 Hz for superficial, non-invasive recordings. In such a case, the time resolution is in the range of tens of milliseconds. If the synchronization between EEG and events evoking specific brain responses (e.g. P300 response for a determined action happening in virtual environments) fails, then it is not possible to relate the brain response to the particular event that elicited it.

(e) Functional re-innervation training to use a sophisticated neuroprosthesis device by an amputee patient: A hybrid brain-computer interface (BCI) system coupled with FES and sub-cutaneous stimulation may be used in elaborating and optimizing functional re-innervation into residual muscles around stumps or other body parts of an amputees. For optimal results, it is important to have high quality synchronization between the sensor data and stimulation data for generating precise stimulation parameters.

In non-medical applications, especially in consumer applications such as gaming or sports activity training, high portability and ease of use of sensing and feedback systems are important factors.

The cost of devices is of course also an important issue in consumer applications. In medical applications the cost of diagnosis or treatment is important, whereby such costs are affected not only by the cost of devices used per se, but also the cost of using the devices, including: ease of set up, manipulation and of obtaining and interpreting results; reuse and sterilization.

The placement of EEG electrodes have been widely researched and one of the commonly used models is the so called "10-20 electrode placement system". Conventional head-mounted electroencephalogram (EEG) sensing devices used in medical or research applications typically comprise a textile cap with a plurality of sensors clipped to the cap. The cap typically is provided with orifices or other fixing means in the positions corresponding to the electrode placement model used. The electrodes are then wired to an amplifying and computing device. Chin straps are provided to stably and accurately adjust and position the cap so that the electrodes are correctly positioned and pressed against the user's head. The positioning of the cap, connection of electrodes and the chip strap or other fixing devices render such conventional systems uninteresting for many consumer applications and tedious even for medical applications. Drawbacks include: not visually aesthetic; overheating of the electrode contact due to reduced air-flow; time-consuming placement of the cap because of adjustments to anatomical inion-nasion distance to ensure 10-20 system and complex set-up (e.g., placement of electrodes, contacts, connectivity etc.); the need for separate electronics and cap electrodes to allow washing of the electrodes.

A medical EEG head cap that avoids individual wire connections by mounting and connecting electrodes to a flexible circuit is disclosed in U.S. Pat. Nos. 4,967,038 and 5,038,782. Another medical EEG headpiece with elastic straps is disclosed in EP0541393. All three of these prior systems suffer from many of the drawbacks mentioned above.

Further EEG head-mounted devices are disclosed in US 2015/0011857, US 2013/0172721, WO 2013/124366, US2011/0282231, and US2013/0303874, however that also suffer at least some of the drawbacks including the difficultly to adjust for different head sizes, non-optimal placement of electrodes, difficulty to allow washing of the electrodes/head set for re-use, discomfort to wear and/or high manufacturing costs.

SUMMARY OF THE INVENTION

It is an aim of the invention to provide a brain activity measurement and feedback system that is convenient and comfortable to wear, reliable, and simple to use.

It would be advantages to provide a system that is easily washable and sterilizable.

It would be advantageous to provide a system that saves time for placement and operation.

It would be advantageous to provide a brain activity measurement and feedback system that may be adapted for home use, for ambulatory applications, or for mobile applications.

It would be advantageous to provide a system which is cost effective to manufacture and to use.

It would be advantageous to provide a brain activity measurement and feedback system that provides a user with a virtual or augmented reality environment that can be utilized to improve the response of the cognitive and sensory motor system, for instance in the treatment of brain damage or in the training of motor skills.

It would be advantageous to provide a physiological parameter measurement and motion tracking system (e.g., movements head and body) that ensures accurate real time integration of measurement and control of physiological stimuli and response signals.

It would be advantageous to provide a brain activity measurement and feedback system that can generate a plurality of stimuli signals of different sources (e.g. visual, auditive, touch sensory, electric, magnetic) and/or that can additionally measure a plurality of physiological response signals of different types (e.g. body part movement, eye movement, galvanic skin response).

It would be advantageous to reduce electrical interference among the input modules (measurements) and output modules (stimuli) and system operation.

It would be advantageous to easily adapt the system to various head and body sizes.

It would be advantageous to provide a more immersive VR experience.

It would be advantageous to ensure high quality electrical or electrochemical contact between skin and electrode tip.

It would be advantageous not to have to remove an electrode sensing net when a user needs to take-off a head-mounted display assembly in order to maintain electrical or electrochemical contacts are maintained.

Disclosed herein is a head set comprising an EEG sensing device comprising EEG sensors configured to be mounted on a head of a wearer so as to position the EEG sensors at selected positions of interest over the wearers scalp. The EEG sensing device comprises a sensor support and a flexible electronic circuit assembled to the sensor support, the EEG sensors connected to the flexible electronic circuit. The sensor support and flexible circuit comprise a central stem configured to extend along a center plane of the top of the head in a direction from nasion to inion, a front lateral branch extending laterally from the central stem configured to extend across a front portion of a wearer's head, a center lateral branch extending laterally from the central stem configured to extend across a top portion of a wearer's head essentially between the wearer's ears, and a rear lateral branch extending laterally from the central stem configured to extend across a back portion of a wearer's head.

According to a first aspect of the invention, the sensor support comprises a base wall and side walls extending along edges of the base wall to form an essentially flat "U" shaped channel in which the flexible circuit is assembled.

According to a second aspect of the invention, especially for embodiments using wet electrodes, the flexible circuit comprises orifices adjacent the EEG sensor contacts or electrodes, wherein the EEG sensor orifices overlap the flexible circuit orifices such that a through passage between a top surface and a bottom surface of the sensor support is provided to allow conductive gel to be inserted from a top side of the head set while it is positioned on a wearer's head.

The through passages could also serve, alternatively or in addition, as access passages for inserting complementary electrodes or other sensors, for instance to test or calibrate the electrodes of the head set, or to add additional sensors or stimulation devices, such as temperature sensors and NIRS, tDCS, tRNS, tACS devices. In a particular embodiment, the through passages may advantageously be used for access by Near Infrared Light emitters and receivers (NIRS) placed over or in these through passages or in other extra orifices. Near Infrared spectroscopy can be very useful to measure blood oxygen levels of the brain tissue. This way one can co-register the electrical and blood-oxygen levels.

Each of the lateral branches further comprises extensions extending in a front to rear, or in a rear to front direction. The EEG sensors are positioned in discrete spaced apart positions along the stem, branches and extensions, for instance in positions according to the international 10-20 system, or according to other EEG positioning systems.

According to a third aspect of the invention, the center lateral branches comprise extensions extending both in a front to rear and in a rear to front direction such that the center lateral branches can be tensioned to both the front lateral branches and the rear lateral branches.

In a preferred embodiment a flexible sealing material is filled over the flexible circuit in the channel in order to seal the electrical circuit tracks and components on the flexible circuit within the channel.

In a preferred embodiment the sensor support is a single piece part.

In a preferred embodiment the sensor support is molded or formed from a flexible polymeric material.

In a preferred embodiment the flexible circuit comprises a single piece flexible substrate.

The head set sensor support may further comprise tensioner anchors configured to anchor elastic tensioners between positions in the stem, branches and extensions of the EEG sensing device, and also between the EEG sensing device and a head mount frame support.

A base wall of the sensor support comprises EEG sensor orifices to allow access to the EEG sensor contacts or electrodes on the flexible circuit.

In an advantageous embodiment, each EEG sensor on the flexible circuit is positioned a discrete EEG signal amplifier configured to amplify the brain electrical activity signal picked up by the corresponding EEG sensor. The EEG sensor may comprise according to the variant, comprise passive or active sensors.

The EEG sensors may comprise electrodes in the form of conductive circuit pads on a surface of a substrate of the flexible circuit intended to face the wearers scalp, or protruding conductive compressible elements mounted on the flexible substrate and electrically connected to a circuit trace of a substrate of the flexible circuit. The EEG sensors may contact the scalp through a wet contact, e.g. using a soft gel, or a semi-solid structure acting in a similar manner to a wet contact, or a dry contact depending on the variant. Furthermore, EEG sensors according to certain variants may not be in direct contact with the scalp, for instance sensors based on near infrared light or capacitive charging In certain embodiments the head set may comprise a head-mounted display (HMD) fixed to a head mount frame support and configured to be positioned over the eyes of a wearer of the headset.

The HMD may comprise a display unit having display means in the form of an electronic screen configured for positioning in front of the wearer's eyes to present visual information to the wearer and optionally further components providing feedback, stimulation or information to the wearer.

The HMD may house various sensing devices and information capture and transmission devices, such as one or more cameras, depth sensors, head movement sensing unit, wireless communication device to interconnect the headset to external electronic devices and computing systems in a wireless fashion, and an on-board power supply for autonomous operation of the head set.

In certain embodiments, the headset may further incorporate a plurality of sensors configured to measure different physiological parameters, selected from a group consisting of Electrocorticogram (ECOG) sensors, eye movement sensors, and head movement sensing unit.

In certain embodiments, the headset may advantageously further incorporate one or a plurality of brain or nerve stimulation devices, for instance Functional Electrical Stimulation (FES) devices, comprising for instance electrodes configured for trans-cranial alternating current stimulation (tACS), direct current stimulation (tDCS), trans-cranial magnetic stimulation (TMS) and trans-cranial ultrasonic stimulation.

In certain embodiments, the headset may further incorporate a position/motion detection system operable to detect a position/motion of a body part of a user, the position/motion/detection system comprising one or more colour cameras, and a depth sensor.

Also disclosed herein is a physiological parameter measurement system comprising a control system, a sensing system, and a stimulation system, the sensing system comprising one or more physiological sensors including at least brain electrical activity sensors mounted in the head set. The stimulation system may comprise one or more stimulation devices including at least a visual stimulation system. The control system may comprising an acquisition module configured to receive sensor signals from the sensing system, and a control module configured to process the signals from the acquisition module and control the generation of stimulation signals to one or more devices of the stimulation system. The control system further comprises a clock module wherein the control system is configured to time stamp signals related to the stimulation signals and the sensor signals with a clock signal from the clock module, enabling the stimulation signals to be synchronized with the sensor signals by means of the time stamps.

The time stamped signals related to the stimulation signals may be content code signals received from the stimulation system.

The system may advantageously comprise a display register configured to receive display content representing a final stage before the display content is activated on the display, the display register being configured to generate a display content code signal for transmission to the control system, a time stamp being attached to the display content code signal by the clock module.

The sensing system may comprise physiological sensors selected from a group comprising Electromyogram (EMG) sensors, Electrooculography (EOG) sensors, Electrocardiogram (ECG) sensors, Inertial Sensors (INS), Body temperature sensor, Galvanic skin sensor, pulse oximetry sensor, and respiration sensors.

The stimulation system may comprise stimulation devices selected from a group comprising audio stimulation device, Functional Electrical Stimulation (FES) devices, and haptic feedback devices, said functional electrical stimulation devices being connected to the control system and operable to electrically stimulate one or more body parts of the user. The FES devices may be selected from a group consisting of electrodes configured to stimulate nerves or muscles, trans-cranial alternating current stimulation (tACS), direct current stimulation (tDCS), trans-cranial magnetic stimulation (TMS) and trans-cranial ultrasonic stimulation.

Each stimulation device may comprise an embedded sensor whose signal is registered by a synchronization device.

The system may further comprise in an embodiment, a robotic system for driving movements of a limb of the user and configured to provide haptic feedback.

The clock module may be configured to be synchronized with clock module of other systems, including external computers.

The system may advantageously comprise an exercise logic unit configured to generate visual display frames including instructions and challenges to the display unit.

The system may advantageously comprise an events manager unit configured to generate and transmit stimulation parameters to the stimulation unit.

Further objects and advantageous features of the invention will be apparent from the claims, from the detailed description, and annexed drawings.

BRIEF DESCRIPTION OF THE DRAWINGS

For a better understanding of the invention, and to show how embodiments of the same may be carried into effect, reference will now be made, by way of example, to the accompanying diagrammatic drawings in which:

FIG. 3b is a detailed schematic diagram of a control system of the system of FIG. 3a;

FIG. 5 is a top view illustrating an arrangement of electroencephalography locations and their nomenclature according to the international 10-20 system;

FIG. 15a is a bottom view of a portion of the headset according to an embodiment of the invention, showing an electrode orifice in detail;

FIG. 15b is a top view of the portion of the headset of FIG. 15a;

FIG. 15c is a cross-sectional view through line A-A of FIG. 15a;

FIG. 15d is a perspective cross-sectional view through line D-D of FIG. 15b;

FIG. 15e is a cross-sectional view of the portion of headset of FIG. 15a mounted on a head of a user.

DETAILED DESCRIPTION OF EXEMPLARY EMBODIMENTS

Figure 1A:
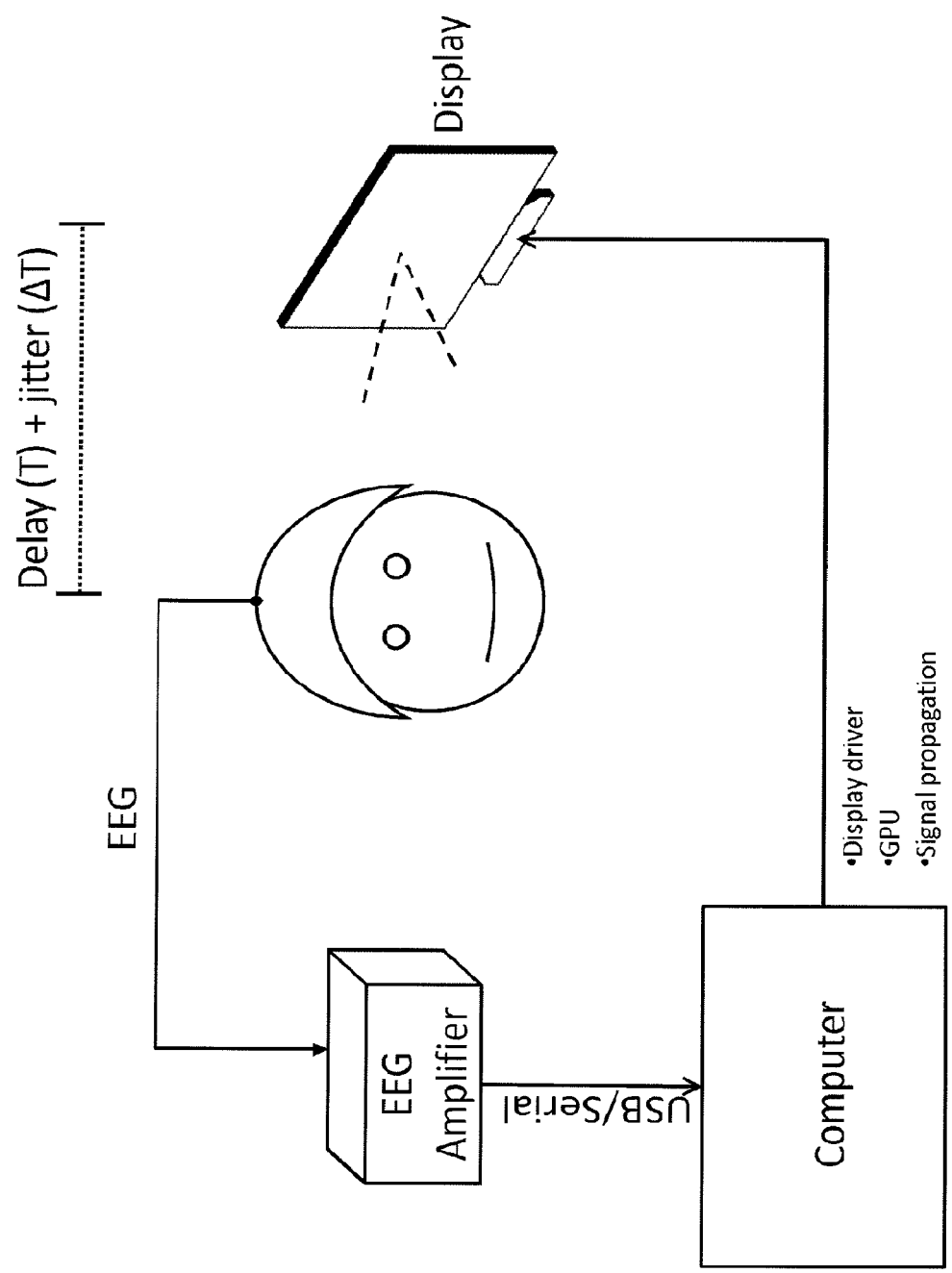
FIGS. 1a and 1b are schematic illustrations of prior art systems.

Referring to the figures, a physiological parameter measurement and motion tracking system according to embodiments of the invention generally comprises a control system 12, a sensing system 13, and a stimulation system 17.

The sensing system comprises one or more physiological sensors including at least brain electrical activity sensors, for instance in the form of electroencephalogram (EEG) sensors

22. The sensing system may comprises other physiological sensors selected from a group comprising Electromyogram (EMG) sensors 24 connected to muscles in user's body, Electrooculography (EOG) sensors 25 (eye movement sensors), Electrocardiogram (ECG) sensors 27, Inertial Sensors (INS) 29 mounted on the user's head and optionally on other body parts such as the users limbs, Body temperature sensor, Galvanic skin sensor. The sensing system further comprises position and/or motion sensors to determine the position and/or the movement of a body part of the user. Position and motion sensors may further be configured to measure the position and/or movement of an object in the field of vision of the user. It may be noted that the notion of position and motion is related to the extent that motion can be determined from a change in position. In embodiments of the invention, position sensors may be used to determine both position and motion of an object or body part, or a motion sensor (such as an inertial sensor) may be used to measure movement of a body part or object without necessarily computing the position thereof. In an advantageous embodiment at least one position/motion sensor comprises a camera 30 and optionally a distance sensor 28, mounted on a head set 2 configured to be worn by the user.

The Stimulation system 17 comprises one or more stimulation devices including at least a visual stimulation system 32. The stimulation system may comprise other stimulation devices selected from a group comprising audio stimulation device 33, and Functional Electrical Stimulation (FES) devices 31 connected to the user (for instance to stimulate nerves, or muscles, or parts of the user's brain e.g. to stimulate movement of a limb), and haptic feedback devices (for instance a robot arm that a user can grasp with his hand and that provides the user with haptic feedback). The stimulation system may further comprise Analogue to Digital Converters (ADC) 37a and Digital to Analogue Converters (DAC) 37b for transfer and processing of signals by a control module 51 of the control system. Devices of the stimulation system may further advantageously comprise means to generate content code signals 39 fed back to the control system 12 in order to timestamp said content code signals and to synchronize the stimulation signals with the measurement signals generated by the sensors of the sensing system.

The control system 12 comprises a clock module 106 and an acquisition module 53 configured to receive content code signals from the stimulation system and sensor signals from the sensing system and to time stamp these signals with a clock signal from the clock module. The control system further comprises a control module that processes the signals from the acquisition module and controls the output of the stimulation signals to devices of the stimulation system. The control module further comprises a memory 55 to store measurement results, control parameters and other information useful for operation of the physiological parameter measurement and motion tracking system.

Figure 3A:
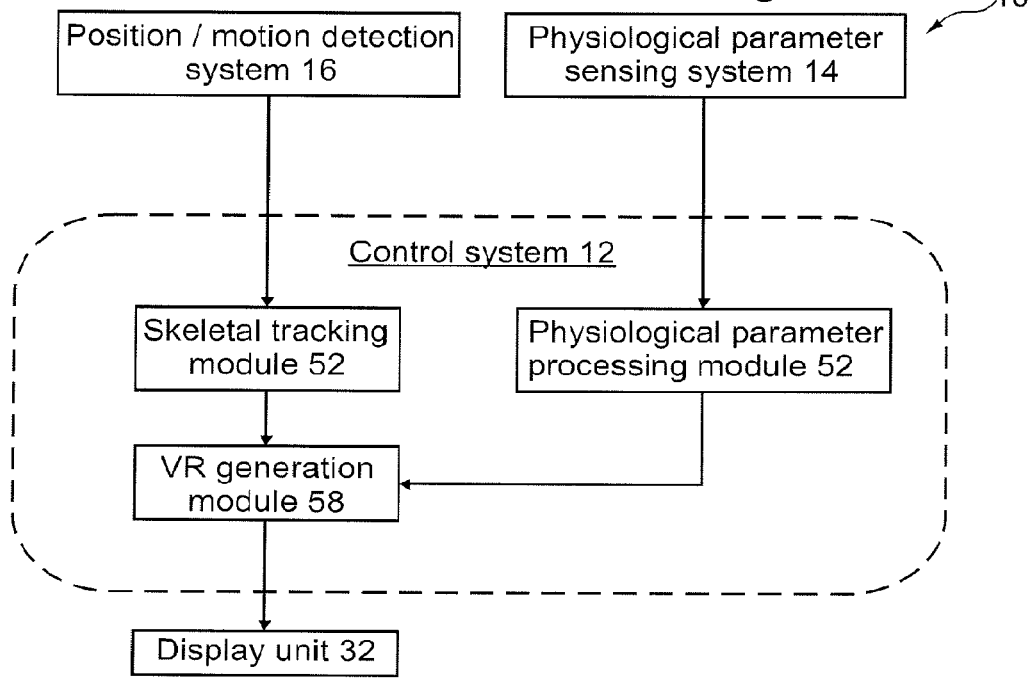
FIG. 3a is a simplified schematic diagram of an embodiment of a physiological parameter measurement system according to the invention.

FIG. 3a is a simplified schematic diagram of a physiological parameter measurement and motion tracking system 10 according to an embodiment of the invention. The system 10 comprises a control system 12 which may be connected to one or more of the following units: a physiological parameter sensing system 14; position/motion detection system 16; and a head set 2, all of which will be described in more detail in the following.

The physiological parameter sensing system 14 comprises one or more sensors 20 configured to measure a physiological parameter of a user. The sensors 20 comprise a plurality of electroencephalogram (EEG) sensors 22 mounted in the head set configured to measure cortical activity of a user by measuring electrical activity in a brain of a user. EEG sensors measure voltage fluctuations result from ionic current flows within the neurons of the brain.

FIG. 5 shows a top view of schematized head showing a known nomenclature of locations for electrode arrangement corresponding to the international 10-20 system, wherein the shaded groups comprise zones of primary interest in many uses of embodiments of the invention.

Figure 4A:
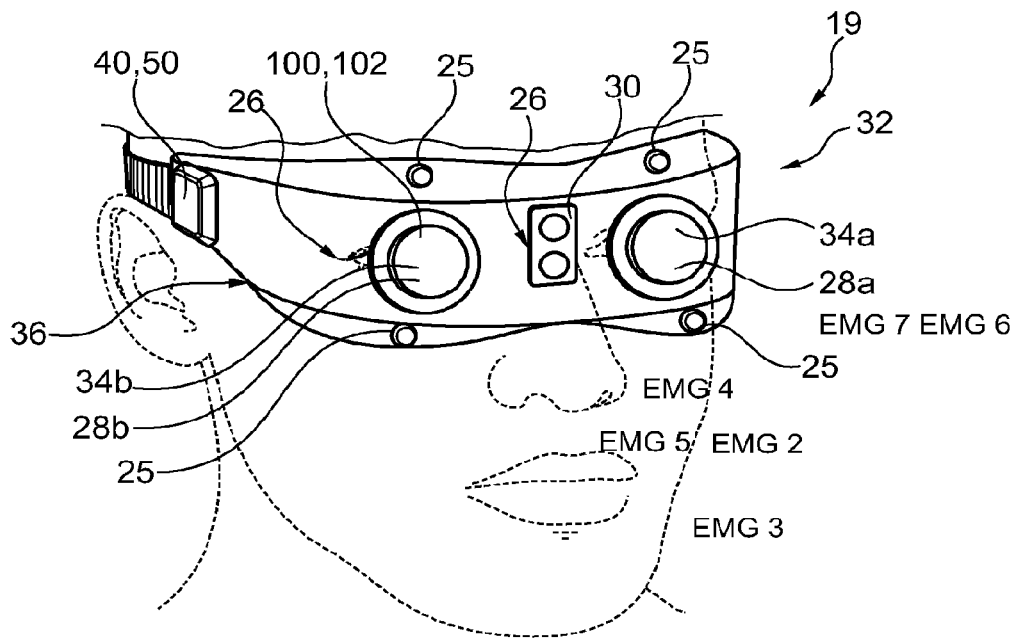
FIG. 4a is a perspective view of an embodiment of a head-mounted display unit of a headset according to an embodiment of the invention.
Figure 4B:
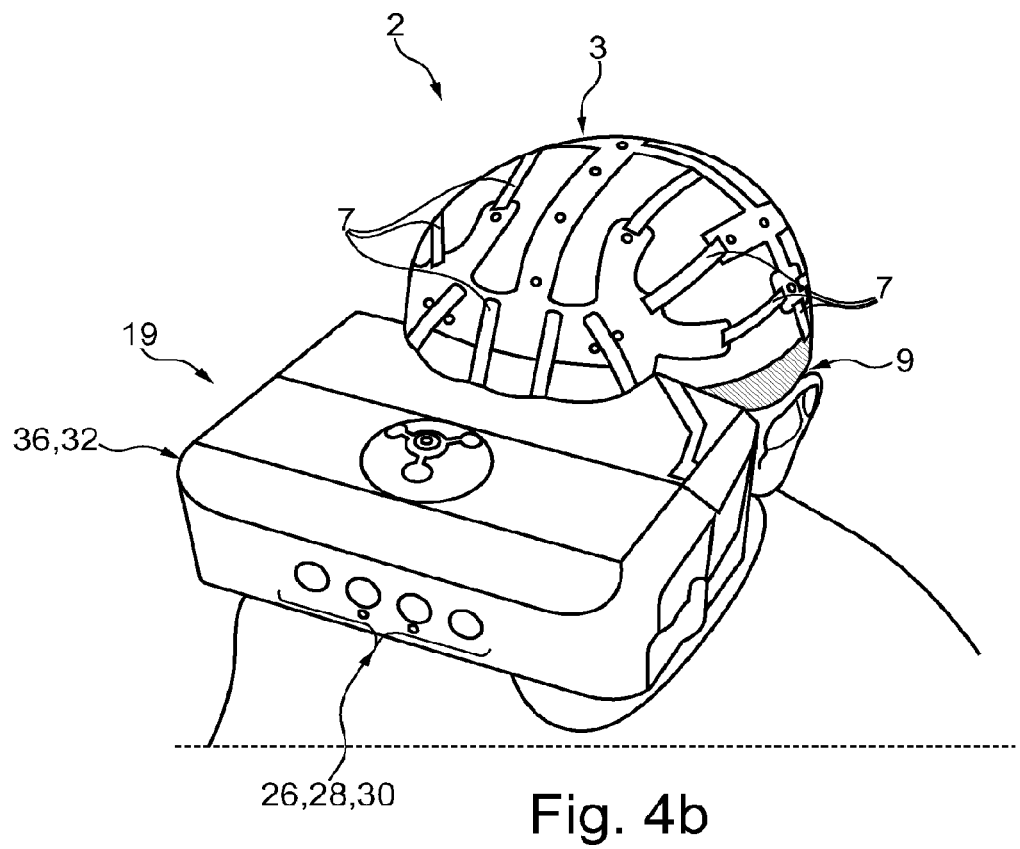
FIGS. 4b and 4c are front and back perspective views of a headset according to an embodiment of the invention, mounted on a head of a user.
Figure 4C:
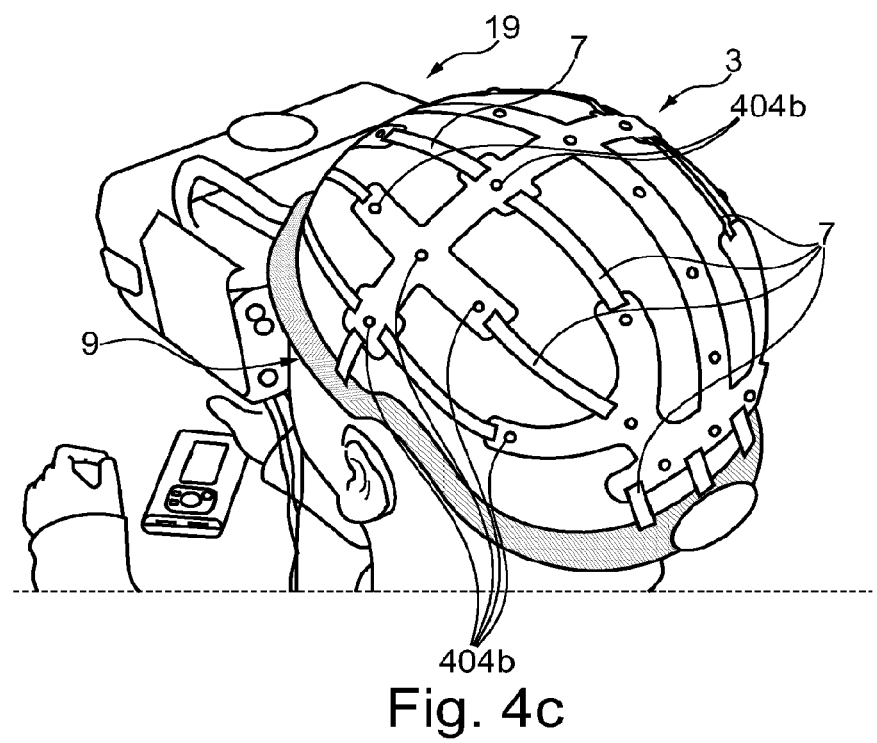

FIGS. 4a, 4b and 4c shows an arrangement of electroencephalogram sensors 22 of a headset according to an embodiment of the invention, positioned on a head of a user.

The head set 2 according to an embodiment of the invention comprises a head mount frame support 9 configure to position and hold the head set on a user's head, and a brain activity (EEG) sensing device 3 attached to the head mount frame support.

The head set may, in certain embodiments, further comprise a head-mounted display 19 fixed to the head mount frame support. The head-mounted display (HMD) 19 is fixed to the head mount frame support and configured to be positioned over the eyes of a wearer of the headset. The HMD 19 may in embodiments be removably attachable to the head mount frame support.

The HMD 19 comprises a display unit 32 mounted in a display unit support 36, the display unit having display means in the form of an electronic screen configured for positioning in front of the wearer's eyes to present visual information to the wearer. The HMD may further comprise other components providing feedback, stimulation or information to the wearer, such as an audio unit 33 to generate sound for the wearer. The HMD may further conveniently house electronics and support further information capture devices such as one or more cameras 30, depth sensors 28, microphone, and various sensors such as a head movement sensing unit 40, 50, an eye gaze sensing unit 100. The HMD may further conveniently house wireless communication devices for wireless communication using any one or more on various known wireless communication protocols to interconnect the headset to external electronic devices and computing systems in a wireless fashion. The HMD may advantageously further house an on-board power supply, in the form of a battery, for autonomous operation of the head set. The head set may also advantageously be provided with one, or a plurality of connectors configured for connecting the head set to external power supply and computing systems or sensors. Further description of various sensors and components of the HMD will be provided further on in this specification.

The EEG sensing device 3 is fixed to the head mount frame support and configured to be positioned over the head of a wearer of the headset so as to position electrodes over the wearers scalp at the selected positions of interest for the application concerned (e.g. for medical applications, for gaming applications, for training applications, for research applications, for brain monitoring applications). In a preferred embodiment the electrode positions correspond to positions known from the international 10-20 system, however other systems may be used and electrode positions refined as a function of the results of research on brain electrical activity.

The EEG sensing device 3 comprises an EEG sensor support 4 and a flexible circuit 6 assembled to the EEG sensor support 4.

The flexible circuit 6 is configured to capture and process brain activity electrical signals and comprises a flexible circuit substrate 601 on or in which are mounted EEG sensors 22 and an EEG signal processing circuit 8 comprising electronic components 8a and circuit traces 8b interconnecting components and sensors and interconnecting the flexible circuit to external power supply and circuits via a connection portion 41 at an end of the flexible circuit. In an advantageous embodiment, the flexible circuit comprises a pluggable electrical connector for plugging to a complementary pluggable electrical connector on the HMD. A pluggable connector 41 is particularly advantageous in that it allows the user to be able take off the HMD without having to remove the electrode head set. This allows the electrical or electrochemical contacts of the electrodes to be maintained in position and undisturbed on the wearer's scalp.

The flexible circuit substrate may advantageously be provided in the form of a thin flexible semi-rigid polymer substrate per se well known in the art of flexible printed circuit technology. The plurality of EEG sensors 22 comprise electrodes spatially positioned on the flexible circuit at the desired electrical brain activity measurement positions, and next to each electrode is positioned a discrete EEG signal amplifier 8b. The close proximity of the amplifier to the electrode allows the brain electrical activity picked up by the electrode to be amplified locally before transmission to a signal analyzing circuit in order to improve the signal to noise ratio of the measured brain activity signals.

The flexible circuit 6 and support 4 of the EEG sensing device are configured such that when they are bent to conforms to a generally spherical or ellipsoid three dimensional form corresponding essentially to the general morphology of a top half of a human head, the EEG sensors are positioned accurately in the desired positions according to the chosen sensor placement. Accuracy and ease of positioning the electrodes correctly and quickly is provided inter alia by the advantageous shape of the sensing device 3, and in particular of the shape of the support 4 and the flexible circuit 6 mounted in the support.

Figure 4D:
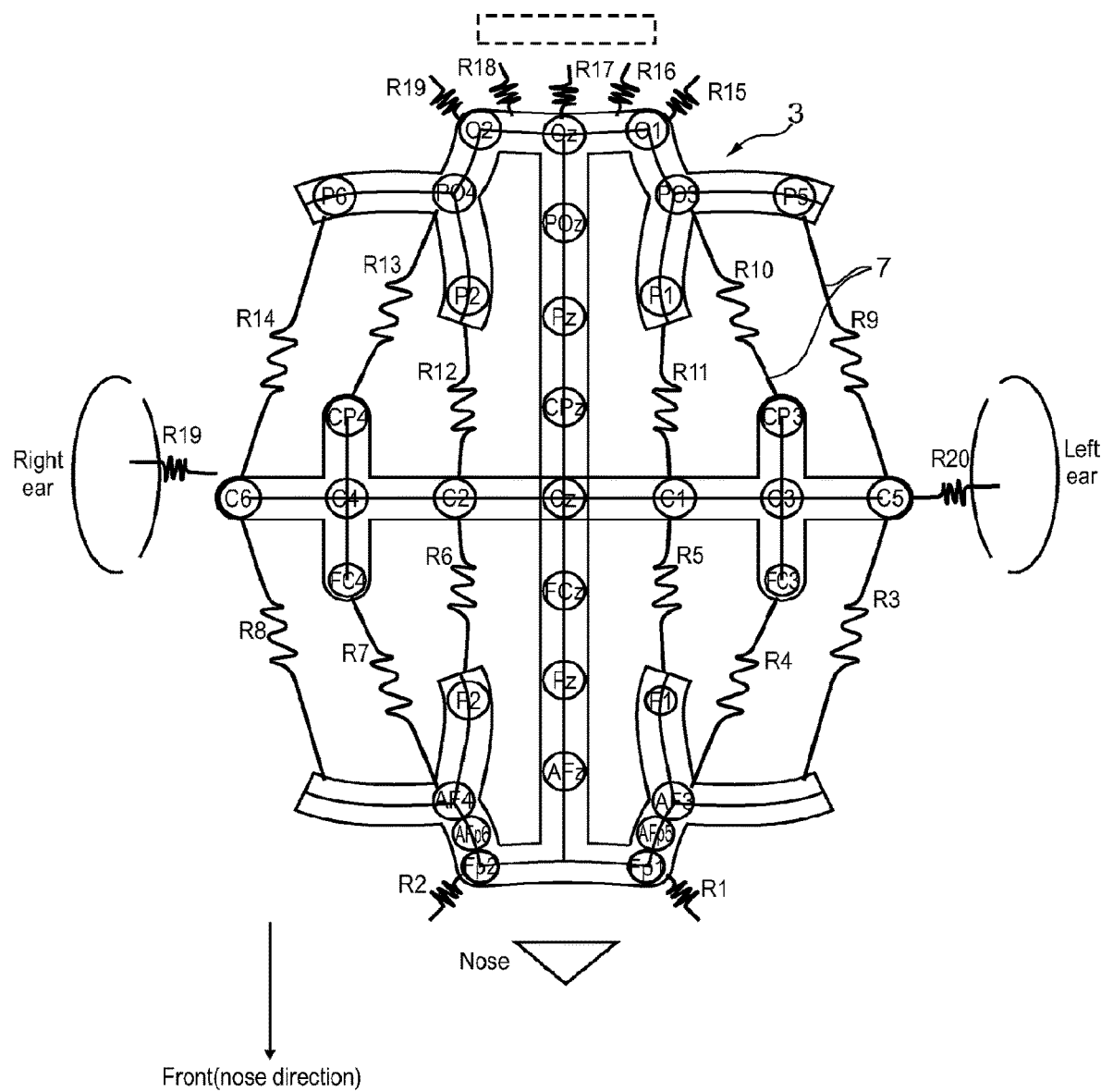
FIG. 4d is a schematic top view of a headset according to an embodiment of the invention, mounted on a head of a user.
Figures 4E, 4F:
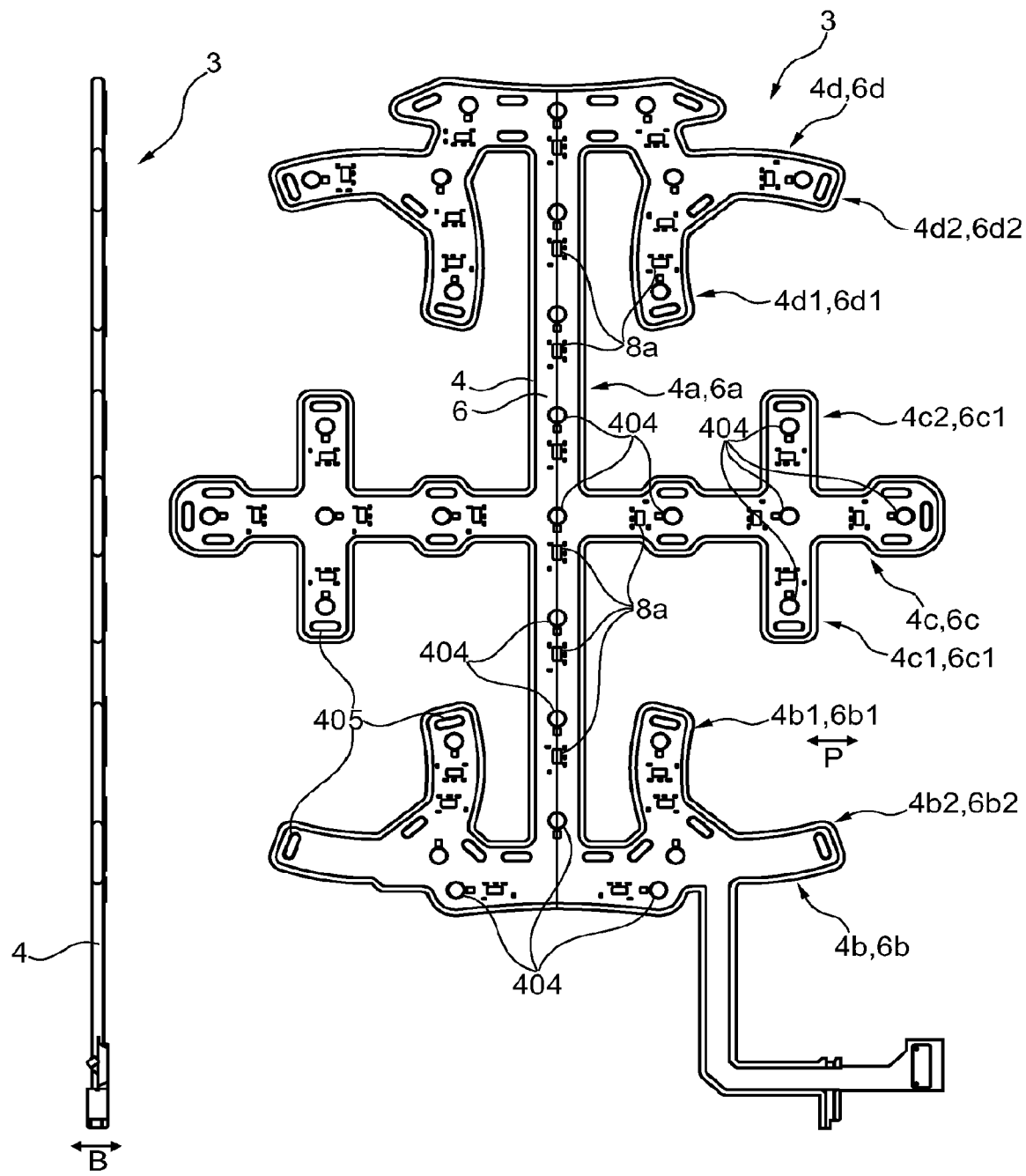
FIGS. 4e and 4f are bottom and side views of an EEG sensing device of a head set according to an embodiment of the invention.
Figure 4H:
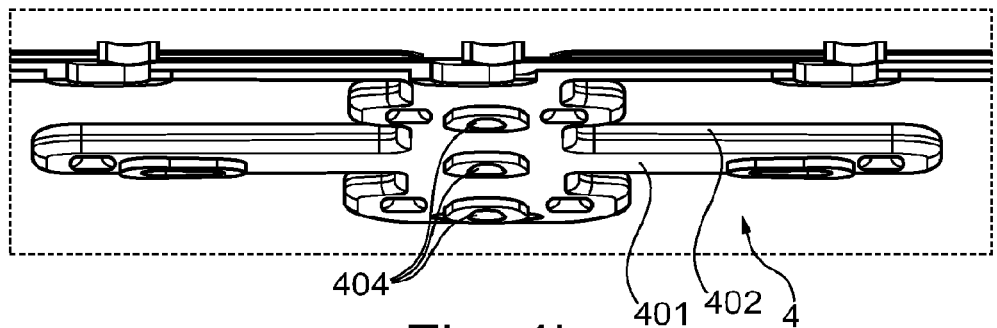
FIGS. 4g and 4h are perspective views of a portion of a support of the EEG sensing device according to an embodiment of the invention.
Figure 4G:
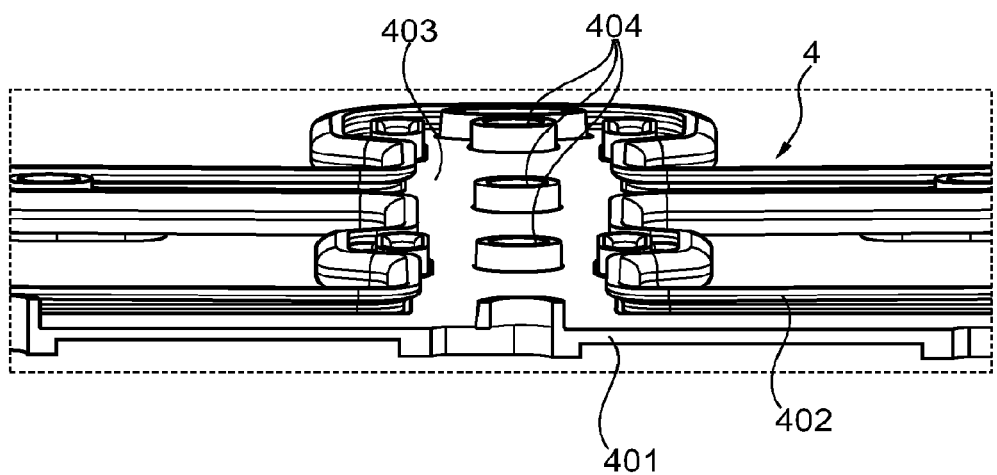
Figure 4I:
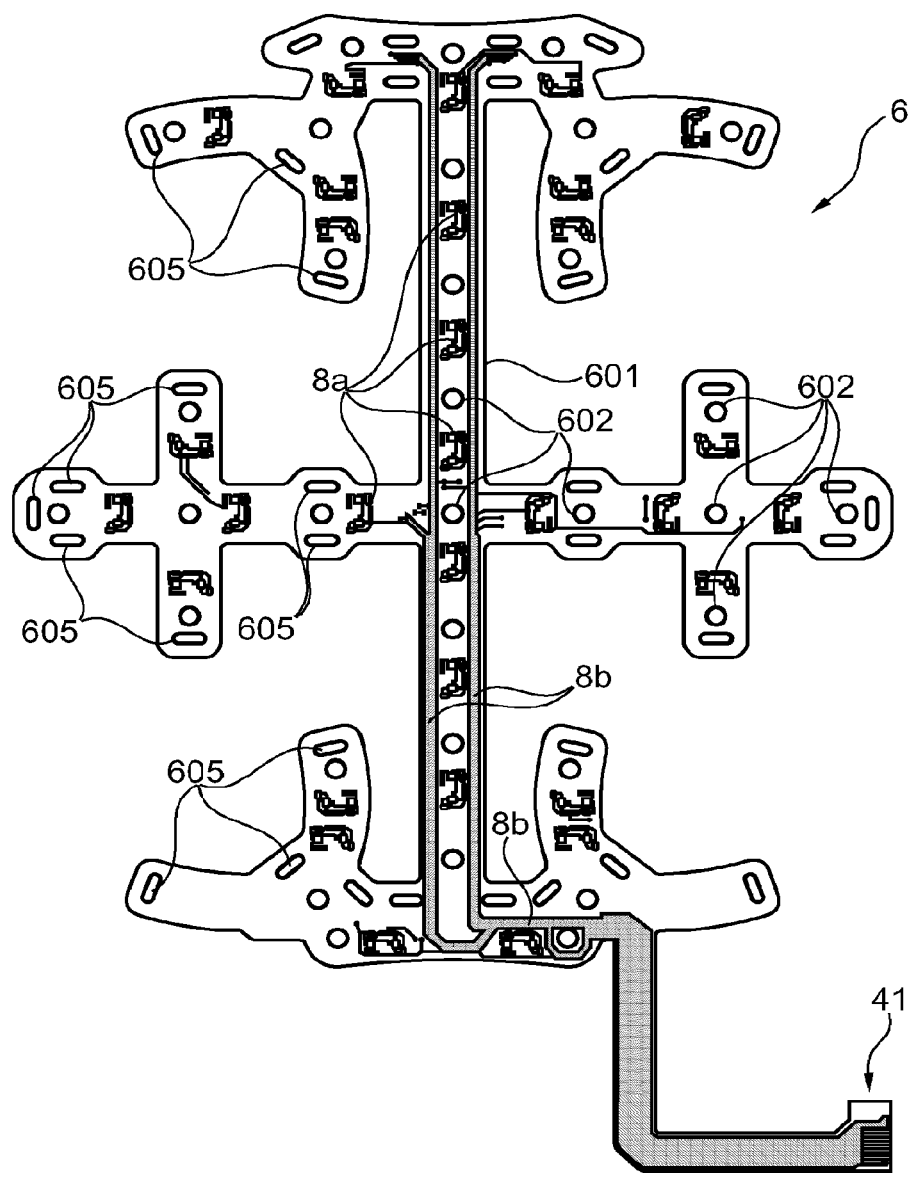
FIG. 4i is a top side view of a flexible circuit of the EEG sensing device according to an embodiment of the invention.
Figure 4J:
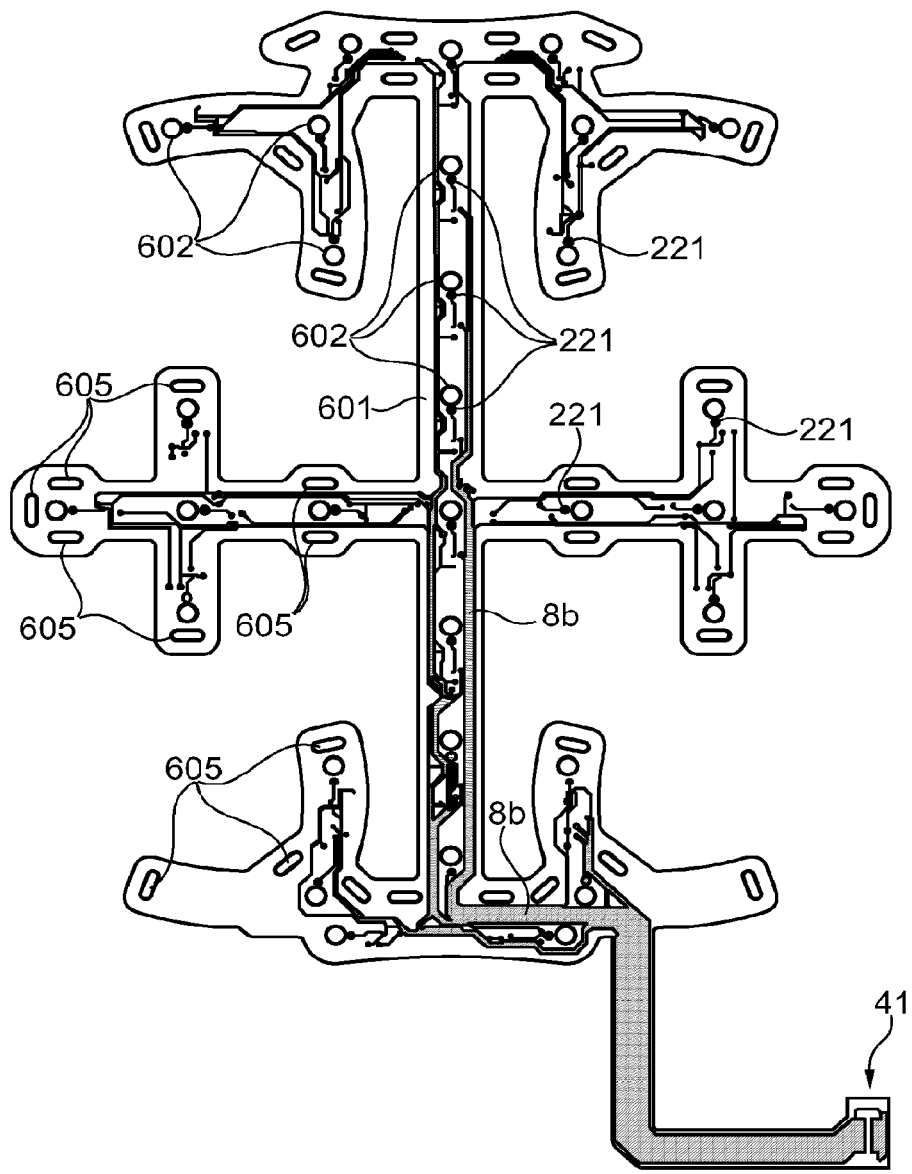
FIG. 4j is a bottom side view of a flexible circuit of the EEG sensing device according to an embodiment of the invention.
Figure 7:
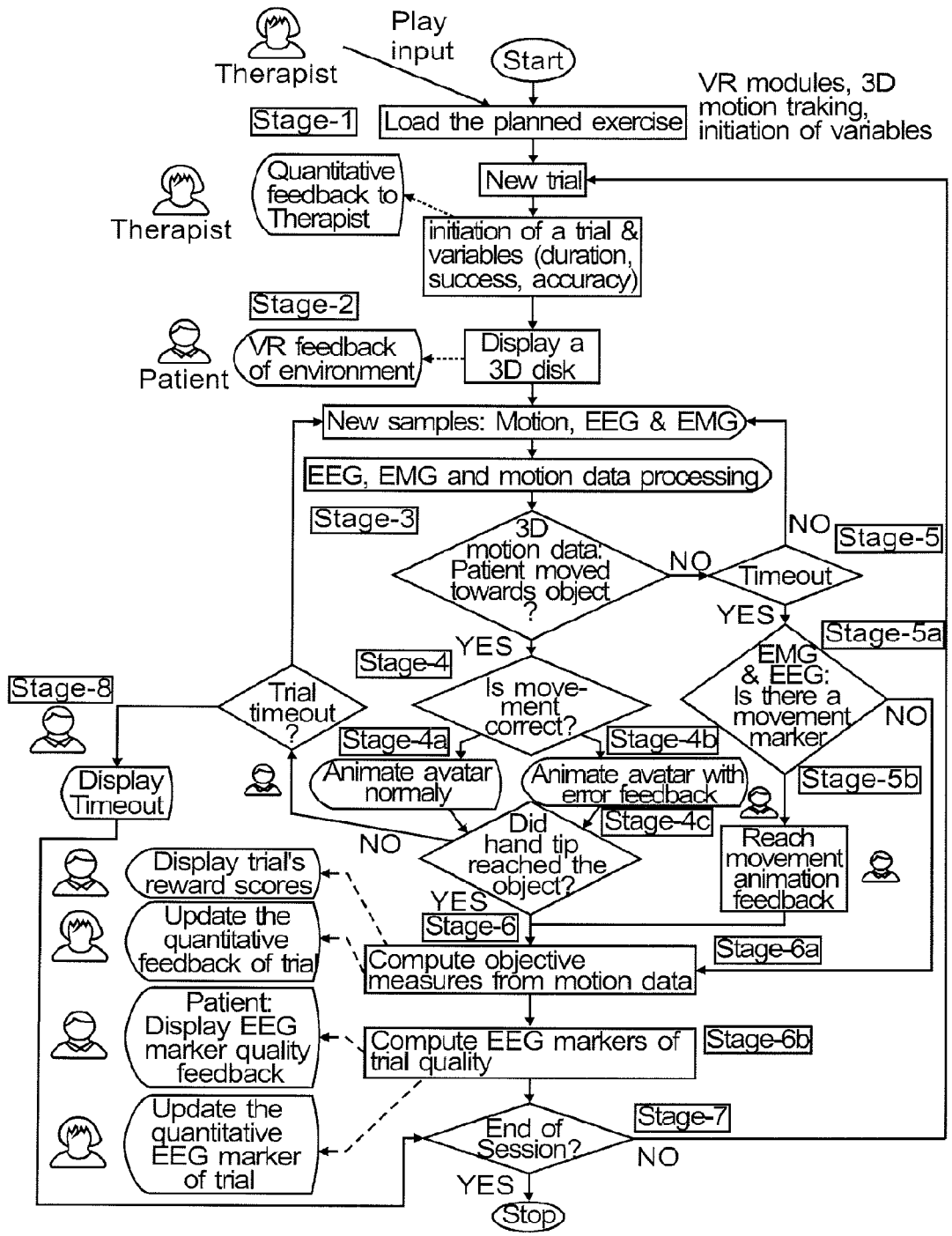
FIG. 7 is a diagrammatic view of a process for training a stroke victim using an embodiment of the system.

In an advantageous embodiment the support comprises a central stem 4a configured to extend along a center plane of the top of the head in a direction from a nose to a centre of the back of a wearers head, and extending laterally from the central stem 4a, a front lateral branch 4b configured to extend across a front portion of a wearer's head, a center lateral branch 4c configured to extend across a top portion of a wearer's head essentially between the wearer's ears, and a rear lateral branch 4d configured to extend across a back portion of a wearer's head. Each of the lateral branches further comprise extensions, including back and side extensions 4b1, 4b2, front and rear extensions 4c1, 4c2 and front and side extensions 4d1, 4d2 respectively. The flexible substrate 6 has a shape that conforms to the support and thus comprises a central stem 6a, a front lateral branch 6b, a center lateral branch 6c, and a rear lateral branch 6d that are mounted in corresponding portions of the support. Each of the lateral branches further comprises extensions, including back and side extensions 6b1, 6b2, front and rear extensions 6c1, 6c2 and front and side extensions 6d1, 6d2 respectively that are mounted in corresponding extensions of the support 4. EEG sensors are positioned in discrete spaced apart positions along the stem, branches and extensions. As best illustrated in FIG. 4d, the stem, branches and extensions are configured in this example to position EEG sensors at certain positions of interest according to the international 10-20 system.

The support 4 may advantageously be made of a flexible elastic or semi-rigid material (as opposed to a textile fabric used in conventional caps) that is flexible enough to bend out of its major plane to conform to the rounded shape of a wearer's head, but that has sufficient self-supporting rigidity in conjunction with the flexible circuit substrate mounted therein, in a direction orthogonal to the bending plane, to generally keep its shape between branches. In effect, the thin flexible circuit substrate is very flexible in the direction B perpendicular to the major surface of the substrate but relatively rigid against bending in a direction P parallel to the major surface. In advantageous embodiments the support may be molded in a single piece, for instance injection molded, press die molded, or blow-molded, out of an elastic polymeric material such as a silicon rubber polymer or similar. The support comprises a base wall 401 and side walls 402 extending along edges of the base wall to form an essentially flat "U" shaped channel 403 in which the flexible circuit 6 is inserted. A flexible sealing material 5, for instance a polymeric elastic potting resin or silicon rubber based potting material may be filled over the flexible circuit in the channel, thus forming a top wall of the support, in order to seal the electrical circuit tracks and components on the flexible circuit. This advantageously allows the EEG sensing device 3 of the head set 2 to be resistant to liquids and to be easily washable and if needed sterilizable, without damaging the electronic circuits contained therein. A flexible top wall of a similar or different material to the bottom wall could also be assembled over the flexible circuit and bonded, welded or fastened with mechanical means to the base wall.

As best seen in FIGS. 4g, 4h and 15a-15e, the base wall 401 of the support advantageously comprises EEG sensor orifices 404 to allow access to the EEG sensor contacts or electrodes 221 on the flexible circuit substrate. In an embodiment, the EEG sensor orifices may comprise a first portion 404a below the electrode 221 and a second portion 404b that is aligned with or overlaps an orifice 602 in the flexible circuit, such that a through passage is formed extending from the bottom surface 406 to the top surface 506 of the support 4. The through passage provides access from the top of the sensing device to the scalp of the wearer to inject a conductive gel 37 from the top of the device when the sensing device is mounted on a wearer's scalp. The conductive gel 37 provides a good electrical contact between the wearer's skin and the electrodes 221. Alternatively, a gel- or water-based electrode could be re-wetted by injecting water in the through passages without removing the sensing device. As best illustrated in FIG. 15e, the gel 37 is able to be injected in the second portion 404a of the orifice and spread laterally to fill the second portion 404b of the orifice 404 to contact the electrode 221 arranged on a bottom side of the flexible circuit.

The through passages could also serve, alternatively or in addition, as access passages for inserting complementary electrodes or other sensors, for instance to test or calibrate the electrodes of the head set, or to add additional sensors or stimulation devices, such as temperature sensors and NIRS, tDCS, tRNS, tACS devices. In a particular embodiment, the through passages may advantageously be used for access by Near Infrared Light emitters and receivers (NIRS) placed over or in these through passages or in other extra orifices. Near Infrared spectroscopy can be very useful to measure blood oxygen levels of the brain tissue. This way one can co-register the electrical and blood-oxygen levels.

The support 4 further comprises tensioner anchors 405, for instance in the form of fixing orifices, that allow elastic ties 7 or other forms of elastic tensioners to be anchored between positions in the stem, branches and extensions of the EEG sensing device, and also between the EEG sensing device and the head mount frame support 9. The flexible circuit substrate 601 may be provided with corresponding tensioner orifices 605 aligned with the orifices 405 in the support. The elastic tensioners 7 apply a certain tension in the structure to ensure that the branches and extensions of the sensing device 3 conform in a snug fit to the shape of a wearer's head and further to ensure the correct position of the various EEG sensors 22 on the wearers scalp. In particular, the stem and branch arrangement of the sensing device ensures the correct position of the front, rear and central electrodes, whereby the elastic tensioners allow a certain adjustment in the distance between center and front, and between center and rear, to conform to different head sizes. The sensing device may be provided in various sizes, whereby with three different sizes more than 95% of the range of adult human head sizes may be covered with accurate electrode placement. For children additional sizes may be provided. The different sizes may concern essentially the length of the central stem and central lateral branch. In order to cover most anatomical ranges. Anchors 405 are positioned at extremities of each branch and extension, and also in opposing positions within branches to anchor the opposing end of an elastic tensioner 7 connected to an extremity, as best illustrated for instance in FIGS. 4b, 4c, and 4d. The length of each elastic ties may be pre-adjusted during assembly of the sensing device and thereafter remain fixed lengths, but in some embodiments some or all of the elastic tensioners may be of adjustable lengths. The elastic tensioners may be provided in different forms, for instance in the form of an elastic textile based band.

In an alternative embodiment, some or all of the tensioners 7 could be integrally formed with the support 4 as a single part. For instance some or all of the tensioners could be molded with the support 4, for instance in the same flexible polymeric material as the support. In such embodiment, the elastic tensioners may be provided with a thinner wall or smaller width, or with serpentine sections so as to increase the elasticity of the elastic tensioners in comparison to the support portion. Also, during the forming process of the integral support 4 and tensioners 7 part, different materials may be incorporated in different portions, for instance by overmolding or by welding inserts of another material in the injected or molded main support material, or for instance by dual component injection molding.

The head mount frame support 9 may have various configurations, its function being to support the sensing device under a certain elastic tension (as described above) and as a function of the embodiment, to further support the head-mounted display. In an embodiment, as schematically illustrated, the head mount frame support 9 may comprise a head band with an adjustable diameter to allow a correct fit around a wearer's head, the head band being rigid against bending at least in the pulling direction of the elastic tensioners 7. Other head mount structures including helmet like structures to support the HMD and sensing device may be used within the scope of this invention.

In an advantageous embodiment, the EEG electrode may be in the form of a conductive circuit pad on a surface of the flexible circuit substrate intended to face the wearer's scalp. A liquid or self-supporting conductive gel or solid gel may be position on the electrode for contact with the wearer's scalp. In another embodiment, the conductive bridge between the electrical contact on the flexible circuit substrate and scalp of the wearer may be provided by a conductive bead, stud or other protruding element for a dry electrode or wet electrode contact the against the wearer's scalp. The EEG electrode may also be in the form of a protruding conductive compressible element, for instance a stamped and formed sheet metal contact, mounted on the flexible substrate and electrically connected to a circuit trace of the substrate by crimping, welding, soldering or other per se known techniques for connecting electronic components on a flexible circuit board.

EEG sensors according to variants of the invention may include sensors that do not require any direct electrical contact with the scalp (or skin) and may in particular include sensors based on (i) near infrared light and (ii) capacitive charging, according to the per se known measurement principles discussed below:

(i) Near Infrared Spectroscopy (NIRS) uses the fact that the transmission and absorption of NIR light in human body tissues contains information about haemoglobin concentration changes. When a specific area of the brain is activated, the localized blood volume in that area changes quickly. Optical imaging can measure the location and activity of specific regions of the brain by continuously monitoring blood haemoglobin levels through the determination of optical absorption coefficients. NIRS can be used for non-invasive assessment of brain function through the intact skull in human subjects by detecting changes in blood haemoglobin concentrations associated with neural activity.

(ii) Capacitive electrodes are based on the measurement of charge displacements on the body surface due to brain activity. This change of the charge can in turn affect the charge on a metal plate close to the body. Since this electrical plate does not require direct electrical contact to the body, it can be isolated from the body. The measurement of the capacitive EEG (cEEG) is therefore also possible through the hair. A supersensitive signal amplifier is preferably connected to this plate which amplifies the brain signal and processes it.

Figure 6:
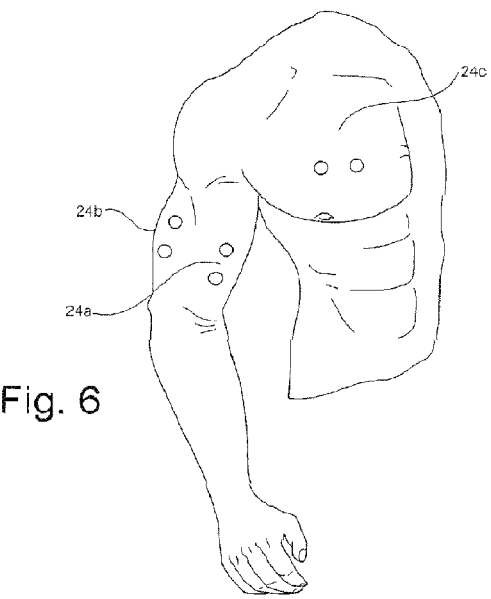
FIG. 6 is a front view of an exemplary arrangement of EMG sensors on a body of a user.

The one or more sensors 20 may additionally comprise sensors 24 configured to measure movement of a muscle of a user, for example by measuring electrical potential generated by muscle cells when the cells are electrically or neurologically activated. A suitable sensor is an electromyogram EMG sensor. The sensors 24 may be mounted on various parts of a body of a user to capture a particular muscular action. For example for a reaching task, they may be arranged on one or more of the hand, arm and chest. FIG. 6 shows an exemplary sensor arrangement, wherein the sensors 24 are arranged on the body in: a first group 24a on the biceps muscle; a second group 24b on the triceps muscle; and a third group 24c on the pectoral muscle.

The one or more sensors 20 may additionally comprise sensors 25 configured to measure electrical potential due to eye movement. A suitable sensor is an electrooculography (EOG) sensor. In an embodiment, as shown in FIG. 4a, there are four sensors that may be arranged in operational proximity to the eye of the user. However it will be appreciated that other numbers of sensors may be used. In an advantageous embodiment the sensors 25 are conveniently connected to a display unit support 36 of the head set, for example they are affixed thereto or embedded therein.

The sensors 20 may alternatively or additionally comprise one or more of the following sensors: electrocorticogram (ECOG); electrocardiogram (ECG); galvanic skin response (GSR) sensor; respiration sensor; pulse-oximetry sensor; temperature sensor; single unit and multi-unit recording chips for measuring neuron response using a microelectrode system. It will be appreciated that sensors 20 may be invasive (for example ECOG, single unit and multi-unit recording chips) or non-invasive (for example EEG). Pulse-oximetry sensor is used for monitoring a patient's oxygen saturation, usually placed on finger tip and may be used to monitor the status of the patient. This signal is particularly useful with patients under intensive care or special care after recovery from cardio-vascular issues. It will be appreciated that for an embodiment with ECG and/or respiration sensors, the information provided by the sensors may be processes to enable tracking of progress of a user. The information may also be processed in combination with EEG information to predict events corresponding to a state of the user, such as the movement of a body part of the user prior to movement occurring. It will be appreciated that for an embodiment with GSR sensors, the information provided by the sensors may be processed to give an indication of an emotional state of a user. For example, the information may be used during the appended example to measure the level of motivation of a user during the task.

In an advantageous embodiment, the head set 2 of the physiological parameter sensing system 14 comprises a wireless transceiver which is operable to wirelessly transfer data to external devices, for instance to a wireless transceiver of the physiological parameter processing module 54, or to a wireless transceiver of the skeletal tracking module 52.

The position/motion detection system 16 comprises one or more sensors 26 suitable for tracking motion of the skeletal structure or a user, or part of the skeletal structure such as an arm. In an advantageous embodiment the sensors comprise one or more cameras which may be arranged separate from the user or attached to the head set 2. At least one, or each camera is arranged to capture the movement of a user and pass the image stream to a skeletal tracking module which will be described in more detail in the following.

In an embodiment the sensors 26 may comprise three cameras: two colour cameras 28a, 28b and a depth sensor camera 30. However, in another embodiment there may be one colour camera 28 and a depth sensor 30. A suitable colour camera may for instance have a resolution of VGA 640×480 pixels and a frame rate of at least 60 frames per second. The field of view of the camera may also be matched to that of the head-mounted display, as will be discussed in more detail in the following. A suitable depth camera may have a resolution of QQ VGA 160×120 pixels.

In an advantageous embodiment two colour cameras 28a and 28b and the depth sensor 30 are arranged on a display unit support 36 of the head set 2 (which is discussed in more detail below) as shown in FIG. 4. The colour cameras 28a, 28b may be arranged over the eyes of the user such that they are spaced apart, for example, by the distance between the pupil axes of a user which is about 65 mm. Such an arrangement enables a stereoscopic display to be captured and thus recreated in VR as will be discussed in more detail in the following. The depth sensor 30 may be arranged between the two cameras 28a, 28b.

Referring to FIGS. 4a-4c the head set 2 comprises a display unit 32 having a display means 34a, 34b for conveying visual information to the user. In an advantageous embodiment the display means 34 comprises a head-up display, which is mounted on an inner side of the display unit in front of the eyes of the user so that the user does not need to adjust their gaze to see the information displayed thereon. The head-up display may comprise a non-transparent screen, such an LCD or LED screen for providing a full VR environment. Alternatively it may comprise a transparent screen, such that the user can see through the display whilst data is displayed on it. Such a display is advantageous in providing an augmented reality AR. There may be two displays 34a, 34b one for each eye, or there may be a single display which is visible by both eyes. The display unit may comprise a 2D or 3D display which may be a stereoscopic display. Although the system is described herein as providing a VR image to a user, it will be appreciated that in other embodiments the image mage be an augmented reality image, mixed reality image or video image.

In the examples of FIGS. 4a-4c the display unit 32 is mounted to a display unit support 36. The display unit support 36 supports the display unit 32 on the user and provides a removable support for the head set 2 on the user. In the example the display unit support 36 extends around the eyes of the user as best seen in FIGS. 4a to 4c.

In an alternative embodiment the display unit 32 may be separate from the head set. For example the display means 34 comprises a monitor or TV display screen or a projector and projector screen.

In an advantageous embodiment the system 10 comprises a head movement sensing unit 40. The head movement sensing unit comprises a movement sensing unit 42 for tracking head movement of a user as they move their head during operation of the system 10. The head movement sensing unit 42 is configured to provide data in relation to the X, Y, Z coordinate location and the roll, pitch and yaw of a head of a user. This data is provided to a head tracking module, which is discussed in more detail in the following, and processes the data such that the display unit 32 can update the displayed VR images in accordance with head movement. For example, as the user moves their head to look to the left the displayed VR images move to the left. Whilst such an operation is not essential it is advantageous in providing a more immersive VR environment. In order to maintain realism it has been found that the maximum latency of the loop defined by movement sensed by the head movement sensing unit 42 and the updated VR image is 20 ms.

In an advantageous embodiment the head movement sensing unit 42 comprises an acceleration sensing means 44, such as an accelerometer configured to measure acceleration of the head. In an advantageous embodiment the sensor 44 comprises three in-plane accelerometers, wherein each in-plane accelerometer is arranged to be sensitive to acceleration along a separate perpendicular plate. In this way the sensor is operable to measure acceleration in three-dimensions. However, it will be appreciated that other accelerometer arrangements are possible, for example, there may only be two in-plane accelerometers arranged to be sensitive to acceleration along separate perpendicular plates such that two-dimensional acceleration is measured. Suitable accelerometers include piezoelectric, piezoresistive and capacitive variants.

In an advantageous embodiment the head movement sensing unit 42 further comprises a head orientation sensing means 47 which is operable to provide data in relation to the orientation of the head. Examples of suitable head orientation sensing means include a gyroscope and a magnetometer 48 which are configured to measure the orientation of a head of a user.

In an advantageous embodiment the head movement sensing unit 42 may be arranged on the head set 2. For example, the movement sensing unit 42 may be housed in a movement sensing unit support 50 that is formed integrally with or is attached to the display unit support 36.

In an advantageous embodiment the system 10 may comprise an eye gaze sensing unit 100. The eye gaze sensing unit 100 comprises one or more eye gaze sensors 102 for sensing the direction of gaze of the user. In an advantageous embodiment the eye gaze sensor 102 comprises one or more cameras arranged in operation proximity to one or both eyes of the user. The or each camera 102 may be configured to track eye gaze by using the centre of the pupil and infrared/near-infrared non-collimated light to create corneal reflections (CR). However, it will be appreciated that other sensing means may be used for example: electrooculogram (EOG); or eye attached tracking. The data from the movement sensing unit 42 is provided to an eye tracking module, which is discussed in more detail in the following, and processes the data such that the display unit 32 can update the displayed VR images in accordance with eye movement. For example, as the user moves their eyes to look to the left the displayed VR images pan to the left. Whilst such an operation is not essential it is advantageous in providing a more immersive VR environment. In order to maintain realism it has been found that the maximum latency of the loop defined by movement sensed by the eye gaze sensing unit 100 and the updated VR image is about 50 ms, however in an advantageous embodiment it is 20 ms or lower.

In an advantageous embodiment the eye gaze sensing unit 100 may be arranged on the head set 2. For example, the eye gaze sensing unit 42 may be attached to the display unit support 36 as shown in FIG. 4a.

The control system 12 processes data from the physiological parameter sensing system 14 and the position/motion detection system 16, and optionally one or both of the head movement sensing unit 40 and the eye gaze sensing module 100, together with operator input data supplied to an input unit, to generate a VR (or AR) data which is displayed by the display unit 32. To perform such a function, in the advantageous embodiment shown in FIGS. 1 and 2, the control system 12 may be organized into a number of modules, such as: a skeletal tracking module 52; a physiological parameter processing module 54; a VR generation module 58; a head tracking module 58; and an eye gaze tracking module 104 which are discussed in the following.

Figure 3B:
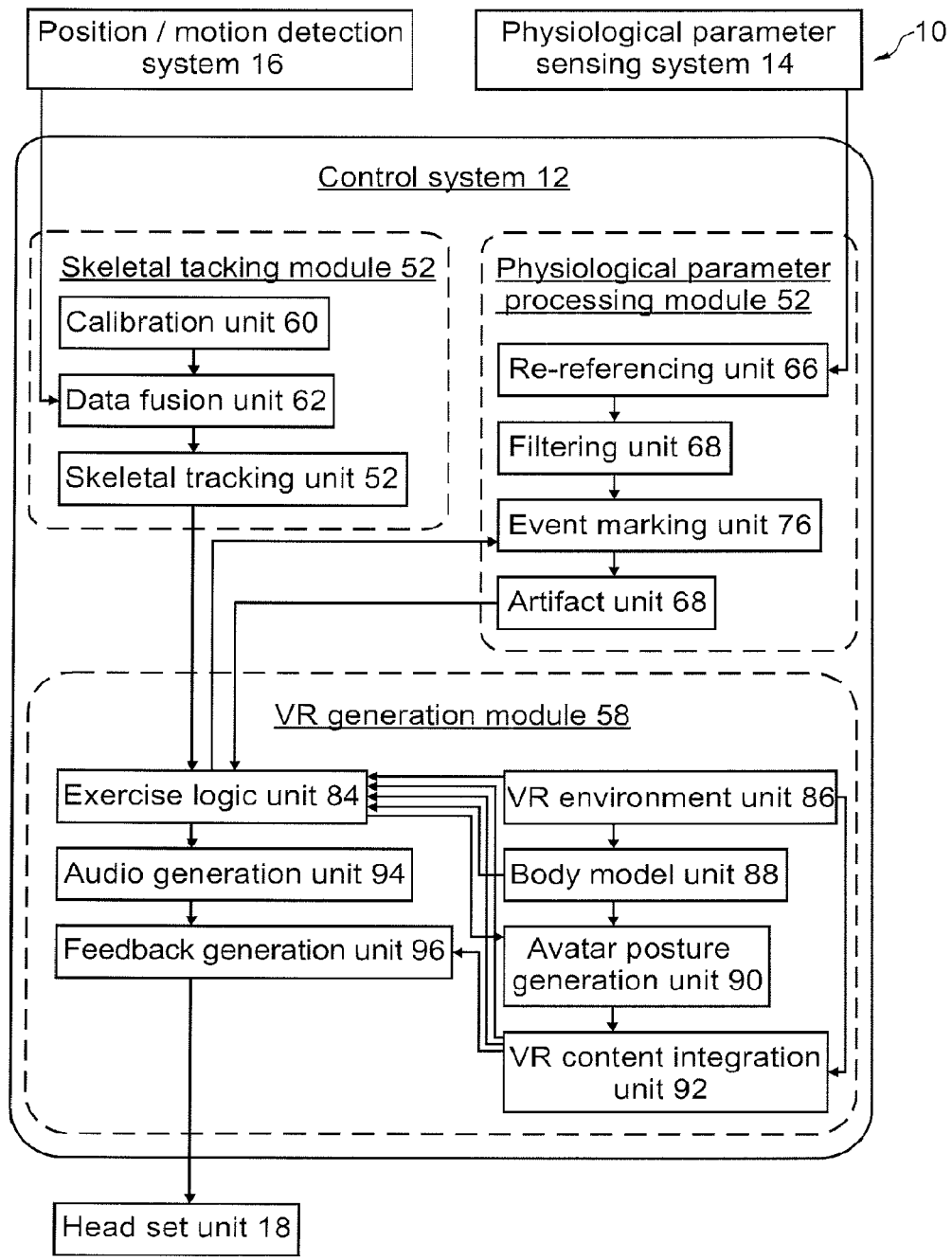

The skeletal tracking module 52 processes the sensory data from the position/motion detection system 16 to obtain joint position/movement data for the VR generation module 58. In an advantageous embodiment the skeletal tracking module 52, as shown in FIG. 3b, comprises a calibration unit 60, a data fusion unit 62 and a skeletal tracking unit 64 the operations of which will now be discussed.

The sensors 26 of the position/motion detection system 16 provide data in relation to the position/movement of a whole or part of a skeletal structure of a user to the data fusion unit 62. The data may also comprise information in relation to the environment, for example the size and arrangement of the room the user is in. In the exemplary embodiment, wherein the sensors 26 comprise a depth sensor 30 and a colour cameras 28a, 28b the data comprises colour and depth pixel information.

The data fusion unit 62 uses this data, and the calibration unit 62, to generate a 3D point cloud comprising a 3D point model of an external surface of the user and environment. The calibration unit 62 comprises data in relation to the calibration parameters of the sensors 26 and a data matching algorithm. For example, the calibration parameters may comprise data in relation to the deformation of the optical elements in the cameras, colour calibration and hot and dark pixel discarding and interpolation. The data matching algorithm may be operable to match the colour image from cameras 28a and 28b to estimate a depth map which is referenced with respect to a depth map generated from the depth sensor 30. The generated 3D point cloud comprises an array of pixels with an estimated depth such that they can be represented in a three-dimensional coordinate system. The colour of the pixels is also estimated and retained.

The data fusion unit 62 supplies data comprising 3D point cloud information, with pixel colour information, together with colour images to the skeletal tracking unit 64. The skeletal tracking unit 64 processes this data to calculate the position of the skeleton of the user and therefrom estimate the 3D joint positions. In an advantageous embodiment, to achieve this operation, the skeletal tracking unit is organized into several operational blocks: 1) segment the user from the environment using the 3D point cloud data and colour images; 2) detect the head and body parts of the user from the colour images; 3) retrieve a skeleton model of user from 3D point cloud data; 4) use inverse kinematic algorithms together with the skeleton model to improve joint position estimation. The skeletal tracking unit 64 outputs the joint position data to the VR generation module 58 which is discussed in more detail in the following. The joint position data is time stamped by a clock module such that the motion of a body part can be calculated by processing the joint position data over a given time period.

Referring to FIGS. 2 and 3, the physiological parameter processing module 54 processes the sensory data from the physiological parameter sensing system 14 to provide data which is used by the VR generation module 58. The processed data may, for example, comprise information in relation to the intent of a user to move a particular body part or a cognitive state of a user (for example, the cognitive state in response to moving a particular body part or the perceived motion of a body part). The processed data can be used to track the progress of a user, for example as part of a neural rehabilitation program and/or to provide real-time feedback to the user for enhanced adaptive treatment and recovery, as is discussed in more detail in the following.

The cortical activity is measured and recorded as the user performs specific body part movements/intended movements, which are instructed in the VR environment. Examples of such instructed movements are provided in the appended examples. To measure the cortical activity, the EEG sensors 22 are used to extract event related electrical potentials and event related spectral perturbations, in response to the execution and or observation of the movements/intended movements which can be viewed in VR as an avatar of the user.

For example the following bands provide data in relation to various operations: slow cortical potentials (SCPs), which are in the range of 0.1-1.5 Hz and occur in motor areas of the brain provide data in relation to preparation for movement; mu-rhythm (8-12 Hz) in the sensory motor areas of the brain provide data in relation to the execution, observation and imagination of movement of a body part; beta oscillations (13-30 Hz) provide data in relation to sensory motor integration and movement preparation. It will be appreciated that one or more of the above potentials or other suitable potentials may be monitored. Monitoring such potentials over a period of time can be used to provide information in relation to the recovery or a user.

Referring to FIG. 5, an exemplary arrangement of sensors 20 is provided which is suitable for measuring neural events as a user performs various sensorimotor and/or cognitive tasks. EEG sensors 22 may advantageously be arranged into groups to measure motor areas in one or more areas of the brain, for example: central (C1-C6, Cz); fronto-central (FC1-FC4, FCZ); centro-pariental (CP3, CP4, CPZ). In an advantageous embodiment contra lateral EEG sensors C1, C2, C3 and C4 are arranged to measure arm/hand movements. The central, fronto-central and centro-pariental sensors may be used for measuring SCPs. EOG sensors 25 may further be provided to measure eye movement signals. In this way the eye movement signals can be isolated and accounted for when processing the signals of other groups to avoid contamination.

In an advantageous embodiment the physiological parameter processing module 54 comprises a re-referencing unit 66 which is arranged to receive data from the physiological parameter sensing system 14 and configured to process the data to reduce the effect of external noise on the data. For example, it may process data from one or more of the EEG, EOG or EMG sensors. The re-referencing unit 66 may comprise one or more re-referencing blocks: examples of suitable re-referencing blocks include mastoid electrode average reference, and common average reference. In the example embodiment a mastoid electrode average reference is applied to some of the sensors and common average reference is applied to all of the sensors. However, it will be appreciated that other suitable noise filtering techniques may be applied to various sensors and sensor groups.

In an advantageous embodiment, the processed data of the re-referencing unit 66 may be output to a filtering unit 68, however in an embodiment without re-referencing unit, the data from the physiological parameter sensing system 14 is fed directly to the filtering unit 68. The filtering unit 68 may comprise a spectral filtering module 70 which is configured to band pass filter the data for one or more of the EEG, EOG and EMG sensors. In respect of the EEG sensors, the data may be band pass filtered for one or more of the sensors to obtain the activity on one or more of the bands: SCPs, theta, alpha, beta, gamma, mu, gamma, and delta. In an advantageous embodiment the bands SCPs (0.1-1.5 Hz), alpha and mu (8-12 Hz), beta (18-30 Hz) delta (1.5-3.5 Hz), theta (3-8 Hz), low gamma (30-100 Hz) and high gamma (above 100 Hz) are filtered for all of the EEG sensors. In respect of EMG and EOG sensors similar spectral filtering may be applied but with different spectral filtering parameters. For example, for EMG sensors spectral filtering of a 30 Hz high pass cut off may be applied.

The filtering unit 66 may alternatively or additionally comprise a spatial filtering module 72. In an advantageous embodiment a spatial filtering module 72 is applied to the SCPs band data from the EEG sensors (which is extracted by the spectral filtering module 70), however it may also be applied to other extracted bands. A suitable form of spatial filtering is spatial smoothing which comprises weighted averaging of neighboring electrodes to reduce spatial variability of the data. Spatial filtering may also be applied to data from the EOG and EMG sensors.

The filtering unit 66 may alternatively or additionally comprise a Laplacian filtering module 74, which is generally for data from the EEG sensors but may also be applied to data from the EOG and EMG sensors. In an advantageous embodiment a Laplacian filtering module 72 is applied to each of the Alpha, Mu and Beta band data of the EEG sensors which is extracted by the spectral filtering module 70, however it may be applied to other bands. The Laplacian filtering module 72 is configured to further reduce noise and increase spatial resolution of the data.

Figure 3C:
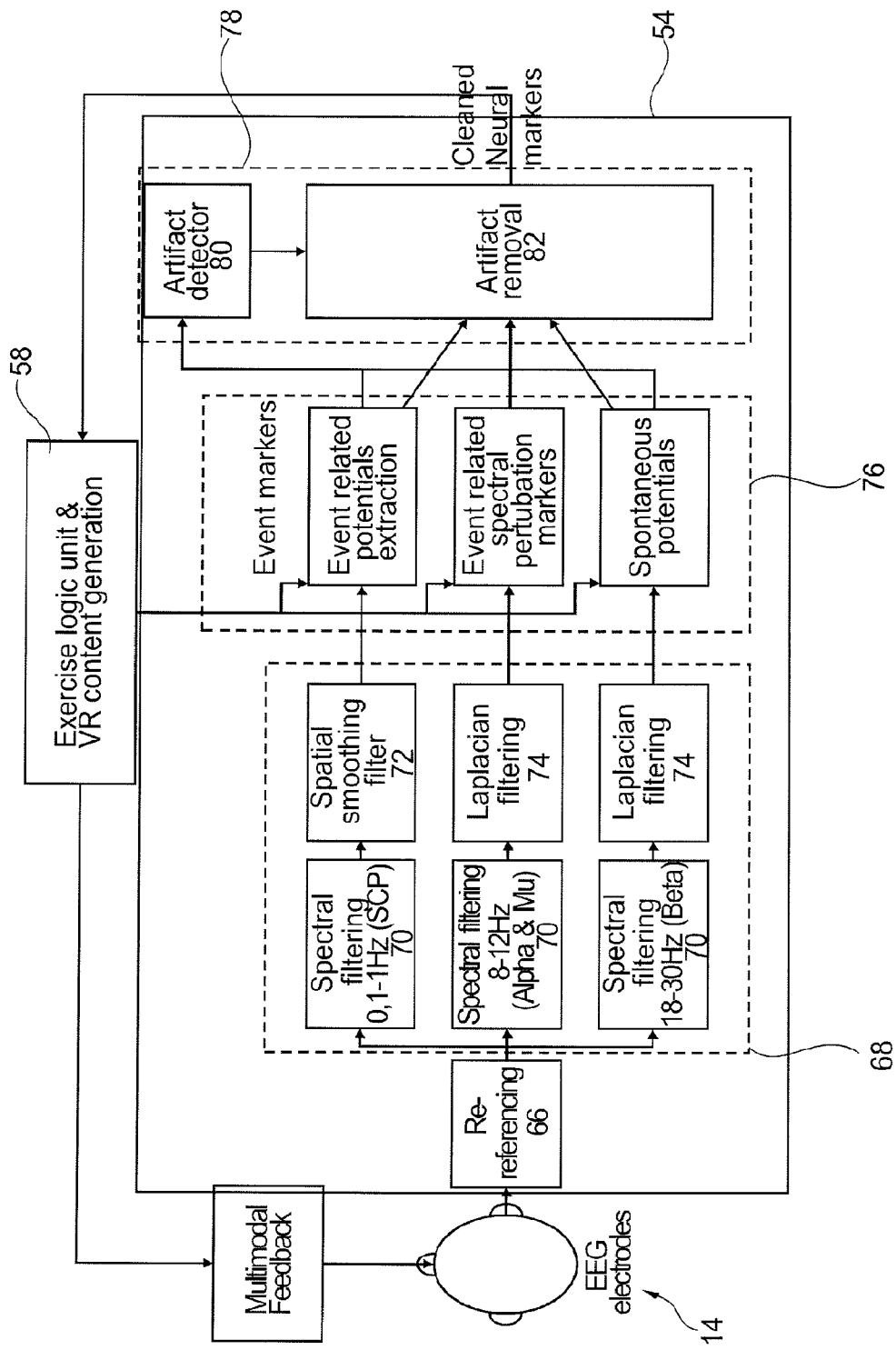
FIG. 3c is a detailed schematic diagram of a physiological tracking module of the control system of FIG. 3b.

The physiological parameter sensing system 14 may further comprise an event marking unit 76. In an advantageous embodiment, when the physiological parameter sensing system 14 comprises a re-referencing unit and/or a filtering unit 68, the event marking unit 76 is arranged to receive processed data from either or both of these units when arranged in series (as shown in the embodiment of FIG. 3c). The event marking unit 76 is operable to use event based makers determined by an exercise logic unit (which will be discussed in more detail in the following) to extract segments of sensory data. For example, when a specific instruction to move a body part is sent to the user from the exercise logic unit, a segment of data is extracted within a suitable time frame following the instruction. The data may, in the example of an EEG sensor, comprise data from a particular cortical area to thereby measure the response of the user to the instruction. For example, an instruction may be sent to the user to move their arm and the extracted data segment may comprise the cortical activity for a period of 2 seconds following instruction. Other example events may comprise: potentials in response to infrequent stimuli in the central and centro-parietal electrodes; movement related potentials that are central SCPs (slow cortical potentials) which appear slightly prior to movement and; error related potentials.

In an advantageous embodiment the event marking unit is configured to perform one or more of following operations: extract event related potential data segments from the SCP band data; extract event related spectral perturbation marker data segments from Alpha and Beta or Mu or gamma band data; extract spontaneous data segments from Beta band data. In the aforementioned, spontaneous data segments correspond to EEG segments without an event marker, and are different to event related potentials, the extraction of which depends on the temporal location of the event marker.

The physiological parameter sensing system 14 may further comprise an artefact detection unit 78 which is arranged to receive the extracted data segments from the event marking unit 76 and is operable to further process the data segments to identify specific artefacts in the segments. For example, the identified artefacts may comprise 1) movement artefacts: the effect of a user movement on a sensor/sensor group 2) electrical interference artefacts: interference, typically 50 Hz from the mains electrical supply 3) eye movement artefacts: such artefacts can be identified by the EOG sensors 25 of the physiological parameter sensing system 14. In an advantageous embodiment the artefact detection unit 78 comprises an artefact detector module 80 which is configured to detect specific artefacts in the data segments. For example, an erroneous segment which requires deleting or a portion of the segment which is erroneous and requires removing from the segment. The advantageous embodiment further comprises an artefact removal module 82, which is arranged to receive the data segments from the event marking unit 76 and artefact detected from the artefact detector module 80 to perform an operation of removing the detected artefact from the data segment. Such an operation may comprise a statistical method such as a regression model which is operable to remove the artefact from the data segment without loss of the segment. The resulting data segment is thereafter output to the VR generation module 58, wherein it may be processed to provide real-time VR feedback which may be based on movement intention as will be discussed in the following. The data may also be stored to enable the progress of a user to be tracked.

In embodiments comprising other sensors, such as ECG, respiration sensors and GSR sensors, it will be appreciated that the data from such sensors can be processed using one of more of the above-mentioned techniques where applicable, for example: noise reduction; filtering; event marking to extract event relate data segments; artefact removal from extracted data segments.

The head tracking module 56 is configured to process the data from the head movement sensing unit 40 to determine the degree of head movement. The processed data is sent to the VR generation module 58, wherein it is processed to provide real-time VR feedback to recreate the associated head movement in the VR environment. For example, as the user moves their head to look to the left the displayed VR images move to the left.

The eye gaze tracking module 104 is configured to process the data from the eye gaze sensing unit 100 to determine a change in gaze of the user. The processed data is sent to the VR generation module 58, wherein it is processed to provide real-time VR feedback to recreate the change in gaze in the VR environment.

Referring now to FIG. 3b, the VR generation module 58 is arranged to receive data from the skeletal tracking module 52, physiological parameter processing module 54, and optionally one or both of the head tracking module 56 and the eye gaze tracking module 104, and is configured to process this data such that it is contextualized with respect to a status of an exercise logic unit (which is discussed in more detail in the following), and to generate a VR environment based on the processed data.

The VR generation module may be organized into several units: an exercise logic unit 84; a VR environment unit 86; a body model unit 88; an avatar posture generation unit 90; a VR content integration unit 92; an audio generation unit 94; and a feedback generation unit 96.

The exercise logic unit 84 is operable to interface with a user input, such as a keyboard or other suitable input device. The user input may be used to select a particular task from a library of tasks and/or set particular parameters for a task.

A body model unit 88 may be arranged to receive data from the exercise logic unit 84 in relation to the particular part of the body required for the selected task. For example this may comprise the entire skeletal structure of the body or a particular part of the body such as an arm. The body model unit 88 thereafter retrieves a model of the required body part, for example from a library of body parts. The model may comprise a 3D point cloud model, or other suitable model.

The avatar posture generation unit 90 is configured to generate an avatar based on the model of the body part from the body part model 88.

In an advantageous embodiment the VR environment unit 86 is arranged to receive data from the exercise logic unit 84 in relation to the particular objects which are required for the selected task. For example the objects may comprise a disk or ball to be displayed to the user.

The VR content integration unit may be arranged to receive the avatar data from the avatar posture generation unit 90 and the environment data from the VR environment unit 86 and to integrate the data in a VR environment. The integrated data is thereafter transferred to the exercise logic unit 58 and also output to the feedback generation unit 86. The feedback generation unit 86 is arranged to output the VR environment data to the display means 34 of the head set 2.

During operation of the task the exercise logic unit 84 receives data comprising joint position information from the skeletal tracking module 64, data comprising physiological data segments from the physiological parameter processing module 54 data from the body model unit 88 and data from the VR environment unit 86. The exercise logic unit 84 is operable to processes the joint position information data which is in turn sent to the avatar posture generation unit 90 for further processing and subsequent display. The exercise logic unit 84 may optionally manipulated the data so that it may be used to provide VR feedback to the user. Examples of such processing and manipulation include amplification of erroneous movement; auto correction of movement to induce positive reinforcement; mapping of movements of one limb to another.

As the user moves, interactions and/or collisions with the objects, as defined by the VR environment unit 86, in the VR environment, are detected by the exercise logic unit 84 to further update the feedback provided to the user.

The exercise logic unit 84 may also provide audio feedback. For example, an audio generation unit (not shown) may receive audio data from the exercise logic unit, which is subsequently processed by the feedback unit 94 and output to the user, for example, by headphones (not shown) mounted to the head set 2. The audio data may be synchronised with the visual feedback, for example, to better indicate collisions with objects in the VR environment and to provide a more immersive VR environment.

In an advantageous embodiment the exercise logic unit 84 may send instructions to the physiological parameter sensing system 14 to provide feedback to the user via one or more of the sensors 20 of the physiological parameter sensing system 14. For example, the EEG 22 and/or EMG 24 sensors may be supplied with an electrical potential that is transferred to the user. With reference to the appended example, such feedback may be provided during the task. For example at stage 5, wherein there is no arm movement an electrical potential may be sent to EMG 24 sensors arranged on the arm and/or EEG sensors to attempt to stimulate the user into moving their arm. In another example, such feedback may be provided before initiation of the task, for instance, a set period of time before the task, to attempt to enhance a state of memory and learning.

In an advantageous embodiment the control system comprises a clock module 106. The clock module is used to assign time information to data and various stages of input and output and processing. The time information can be used to ensure the data is processed correctly, for example, data from various sensors is combined at the correct time intervals. This is particularly advantageous to ensure accurate real-time processing of multimodal inputs from the various sensors and to generate real-time feedback to the user. The clock module may be configured to interface with one or more modules of the control system to time stamp data. For example: the clock module 106 interfaces with the skeletal tracking module 52 to time stamp data received from the position/motion detection system 16; the clock module 106 interfaces with the physiological parameter processing module 54 to time stamp data received from the physiological parameter sensing system 14; the clock module 106 interfaces with the head tracking module 58 to time stamp data received from the head movement sensing unit 40; the clock module 106 interfaces with the eye gaze tracking module 104 to time stamp data received from the eye gaze sensing unit 100. Various operations on the VR generation module 58 may also interface with the clock module to time stamp data, for example data output to the display means 34.

Unlike complex conventional systems that connect several independent devices together, in embodiments of the present invention synchronization occurs at the source of the data generation (for both sensing and stimulation), thereby ensuring accurate synchronization with minimal latency and, importantly, low jitter. For example, for a stereo head-mounted display with refresh rate of 60 Hz, the delay would be as small as 16.7 ms. This is not presently possible with a combination of conventional stand-alone or independent systems. An important feature of the present invention is that it is able to combine a heterogeneous ensemble of data, synchronizing them into a dedicated system architecture at source for ensuring multimodal feedback with minimal latencies. The wearable compact head-mounted device allows easy recording of physiological data from brain and other body parts.

Synchronization Concept:

Latency or Delay (T): It is the time difference between the moment of user's actual action or brain state to the moment of its corresponding feedback/stimulation. It is a positive constant in a typical application. Jitter ($\Delta T$) is the trial to trial deviation in Latency or Delay. For applications that require for instance immersive VR or AR, both latency T and jitter $\Delta T$ should be minimized to the least possible. Whereas in brain computer interface and offline applications, latency T can be compromised but jitter $\Delta T$ should be as small as possible.

Figure 1B:
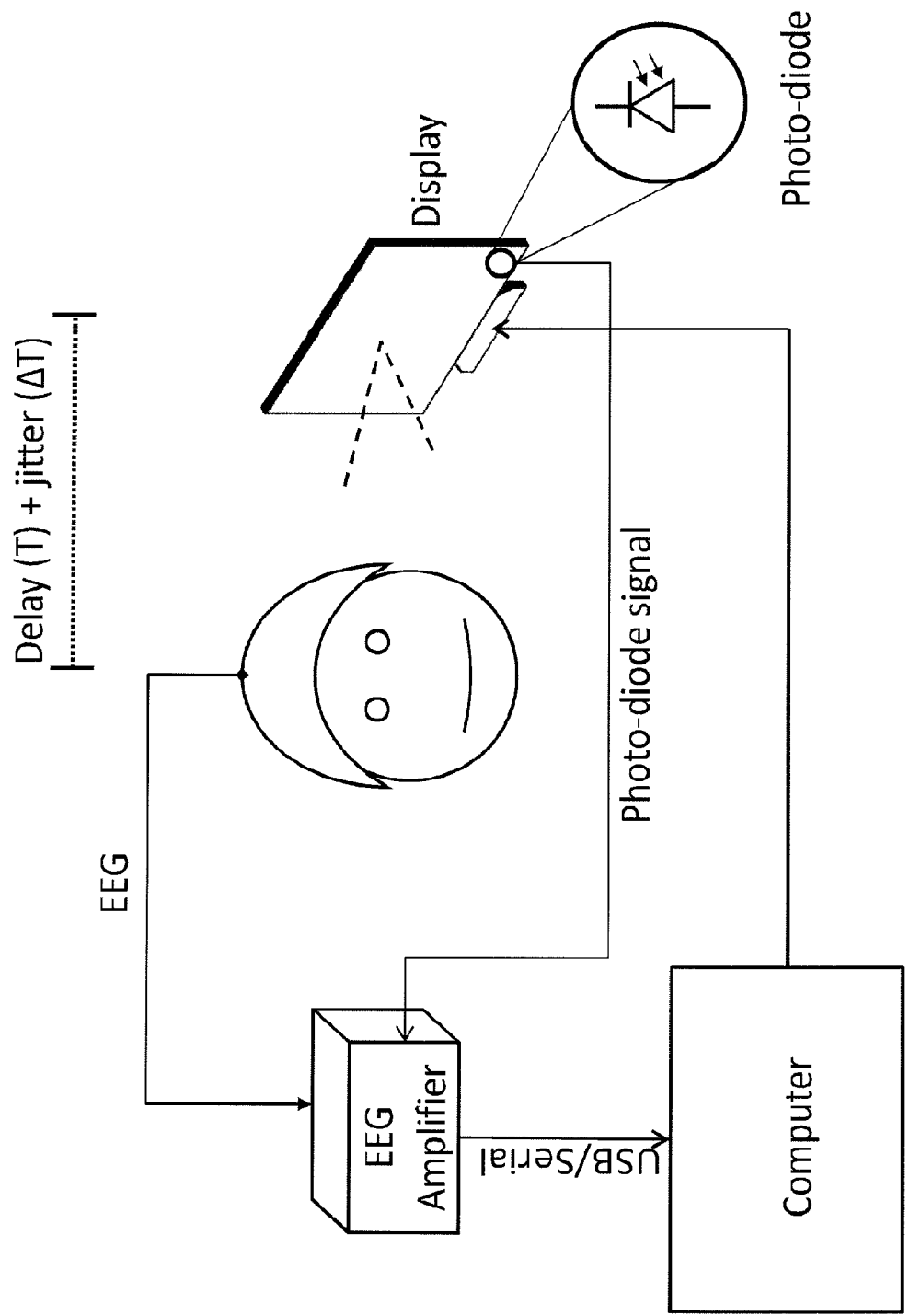

Referring to FIGS. 1a and 1b, two conventional prior-art system architectures are schematically illustrated. In these the synchronization may be ensured to some degree but jitter ($\Delta T$) is not fully minimized.

Design-I (FIG. 1a):

In this design, the moment at which a visual cue is supplied to user is registered directly in the computer while acquiring the EEG signal that is acquired via a USB connection or serial connection. Meaning, the computer assumes, the moment at which it is registered with acquired from user's brain is the moment a cue is displayed to the user. Note that there are inherent delays and jitters in this design. First due to the USB/serial port connectivity to computer, the registration of the sample into computer is has nonzero variable latency. Second, the moment the display command is released from the computer, it undergoes various delay due to underlying display driver, graphical processing unit and signal propagation, which is also not a constant. Hence these two kinds of delays add up and compromise alignment of visually evoked potentials.

Design-II (FIG. 1b):

To avoid the above problem, it is known to use a photo diode to measure the cue and synchronize its signal directly with an EEG amplifier. In this design, usually a photo-diode is placed on the display to sense a light. Usually, a cue is presented to user at the same time a portion of screen where the photo-diode is attached is lighted up. This way the moment at which the cue is presented is registered with photo-diode and supplied to EEG amplifier. This way EEG and visual cue information are directly synchronized at source. This procedure is accurate for alighting visually evoked trials, however has a number of drawbacks:

- the number of visual cues it can code are limited to number of photodiodes. A typical virtual reality based visual stimulation would have large number of events to be registered together with physiological signals accurately.
- the use of photo-diode in a typical micro-display (e.g., 1 square inch size, with pixel density of 800×600) of a head-mounted display would be difficult and even worse reduces usability. Note also that for the photo-diode to function, ample light should be supplied to the diode resulting in a limitation.
- the above drawbacks are further complicated, when a plurality of stimuli (such as audio, magnetic, electrical and mechanical are needed to synchronize with plurality of sensors data (such as EEG, EMG, ECG, video camera, inertial sensors, respiration sensor, pulse oximetry, galvanic skin potentials etc.).

In embodiments of the present invention, the above drawbacks are addressed to provide a system that is accurate and scalable to many different sensors and many different stimuli. This is achieved by employing a centralized clock system that supplies a time-stamp information and each sensor's samples are registered in relation to this to the time-stamp.

In an embodiment, each stimulation device may advantageously be equipped with an embedded sensor whose signal is registered by a synchronization device. This way, a controller can interpret plurality of sensor data and stimulation data can be interpreted accurately for further operation of the system.

In an embodiment, in order to reduce the amount of data to synchronize from each sensor, instead of using a real sensor, video content code from a display register may be read.

Figure 2A:
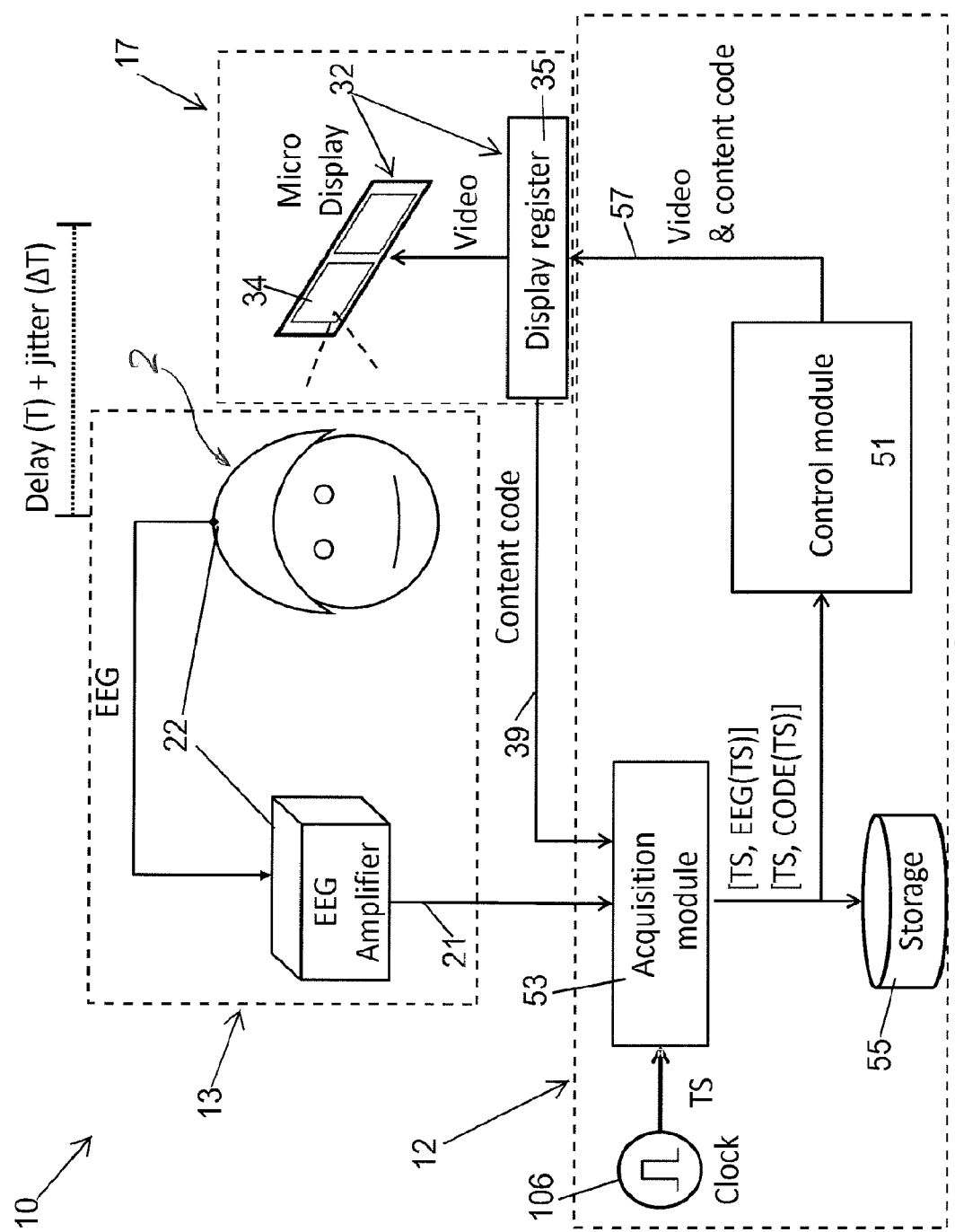
FIG. 2a is a schematic diagram illustrating an embodiment of the invention in which display content displayed to a user is synchronized with response signals (e.g. brain activity signals) measured from the user.

Referring to FIG. 2a, an embodiment of the invention in which the content fed to a micro-display on the headset is synchronized with brain activity signals (EEG signals) is schematically illustrated.

Generally, the visual/video content that is generated in the control system is first pushed to a display register (a final stage before the video content is activated on the display). In our design together with video content, the controller sends a code to a part of the register (say N bits) corresponding to one or more pixels (not too many pixels, so that the user is not disturbed; the corner pixels in the micro display are recommended as they may not be visible to user). The code will be defined by controller describing what exactly the display content is. Now using a clock signal the acquisition module reads the code from the display register and attaches a time stamp and sends to next modules. At the same moment EEG samples are also sampled and attached with the same time stamp. This way when EEG samples and the video code samples are arrived at the controller, these samples could be interpreted accordingly.

Note that all these modules are employed in one embedded system that has a single clock. This leads least latency as well as least jitter.

Figure 2B:
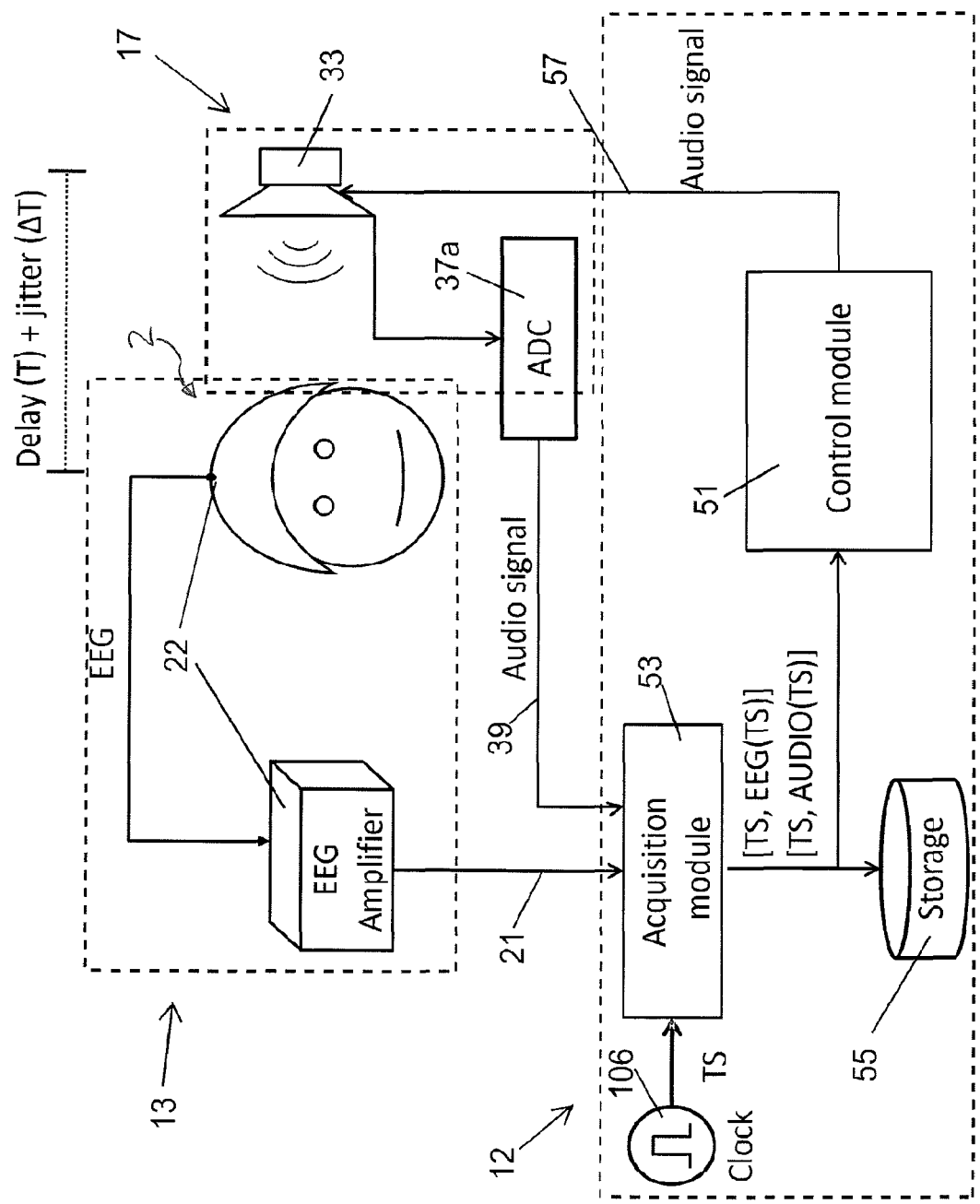
FIG. 2b is a schematic diagram illustrating an embodiment of the invention in which audio content played to a user is synchronized with response signals (e.g. brain activity signals) measured from the user.

The same principle may be used for an audio stimulation as illustrated in FIG. 2b. The audio stimulation can be sampled by the data sent to a digital to analog (DAC) converter.

Figure 2C:
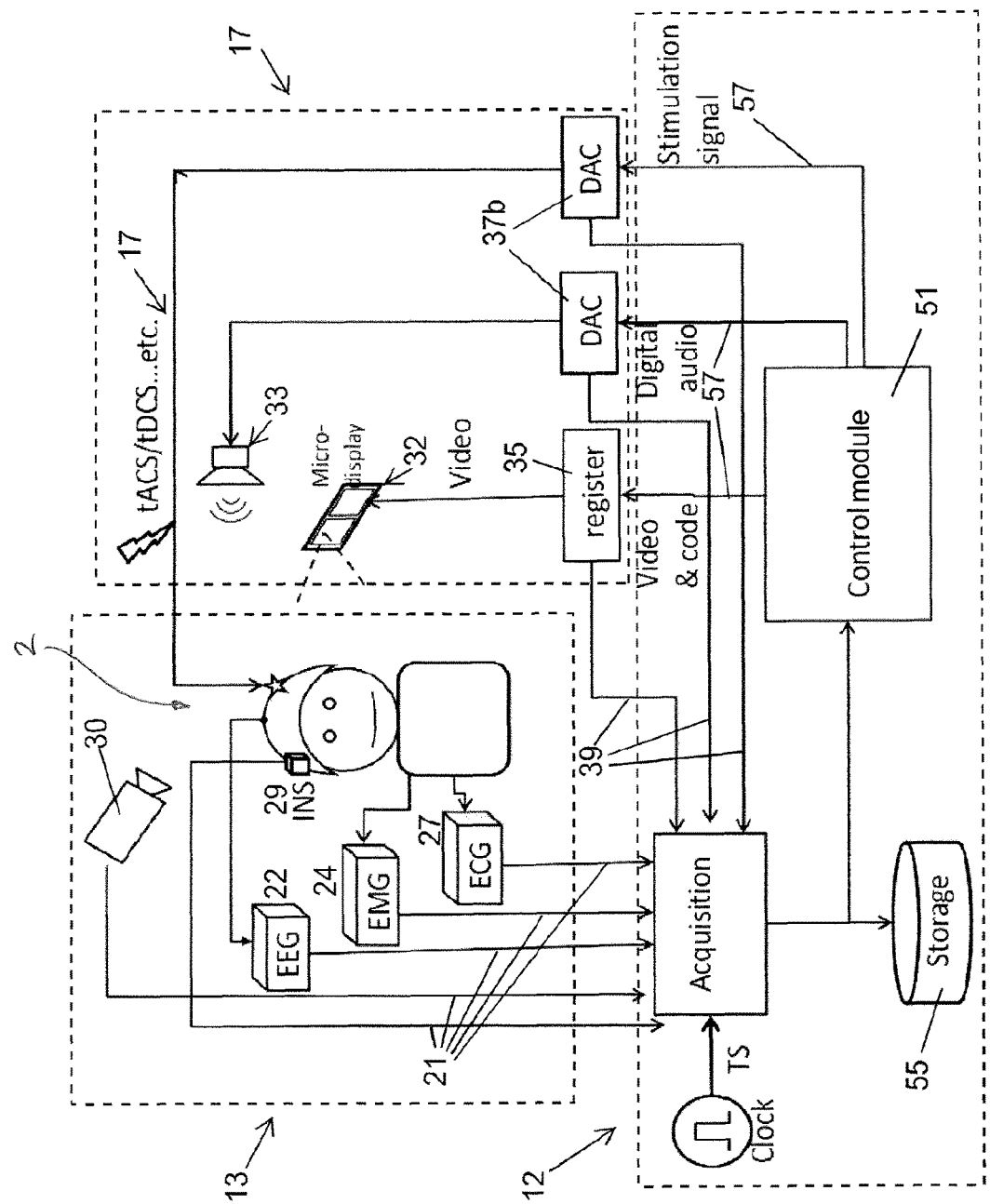
FIG. 2c is a schematic diagram illustrating an embodiment of the invention in which a plurality of signals applied to a user are synchronized with response signals (e.g. brain activity signals) measured from the user.

More generally, any kind of stimulation, as illustrated in FIG. 2c, (such as trans-cranial stimulations (tACS), tDCS, TMS, etc.) could be directed to the acquisition module using a sensor and an analog to digital (ADC) converter. This can also be achieved by sending the digital signals supplied to DAC as illustrated in the case of audio stimulation. Plural data from an EEG, video camera data or any other sensor (e.g. INS: Inertial sensor) is synchronized in the same framework. Note that each sensor or stimulation could be sampled with different sampling frequency. An important point is that the sensor or stimulation data samples are attached with the time-stamp defined with the clock module.

EXAMPLE 1

Operation of System (10) in Exemplary "Reach an Object" Task

In this particular example an object 110, such as a 3D disk, is displayed in a VR environment 112 to a user. The user is instructed to reach to the object using a virtual arm 114 of the user. In the first instance the arm 114 is animated based on data from the skeletal tracking module 16 derived from the sensors of the position/motion detection system 16. In the second instance, wherein there is negligible or no movement detected by the skeletal tracking module 16, then the movement is based data relating to intended movement from the physiological parameter processing module 52 detected by the physiological parameter sensing system 14, and in particular the data may be from the EEG sensors 22 and/or EMG sensors 24.

Figure 8:
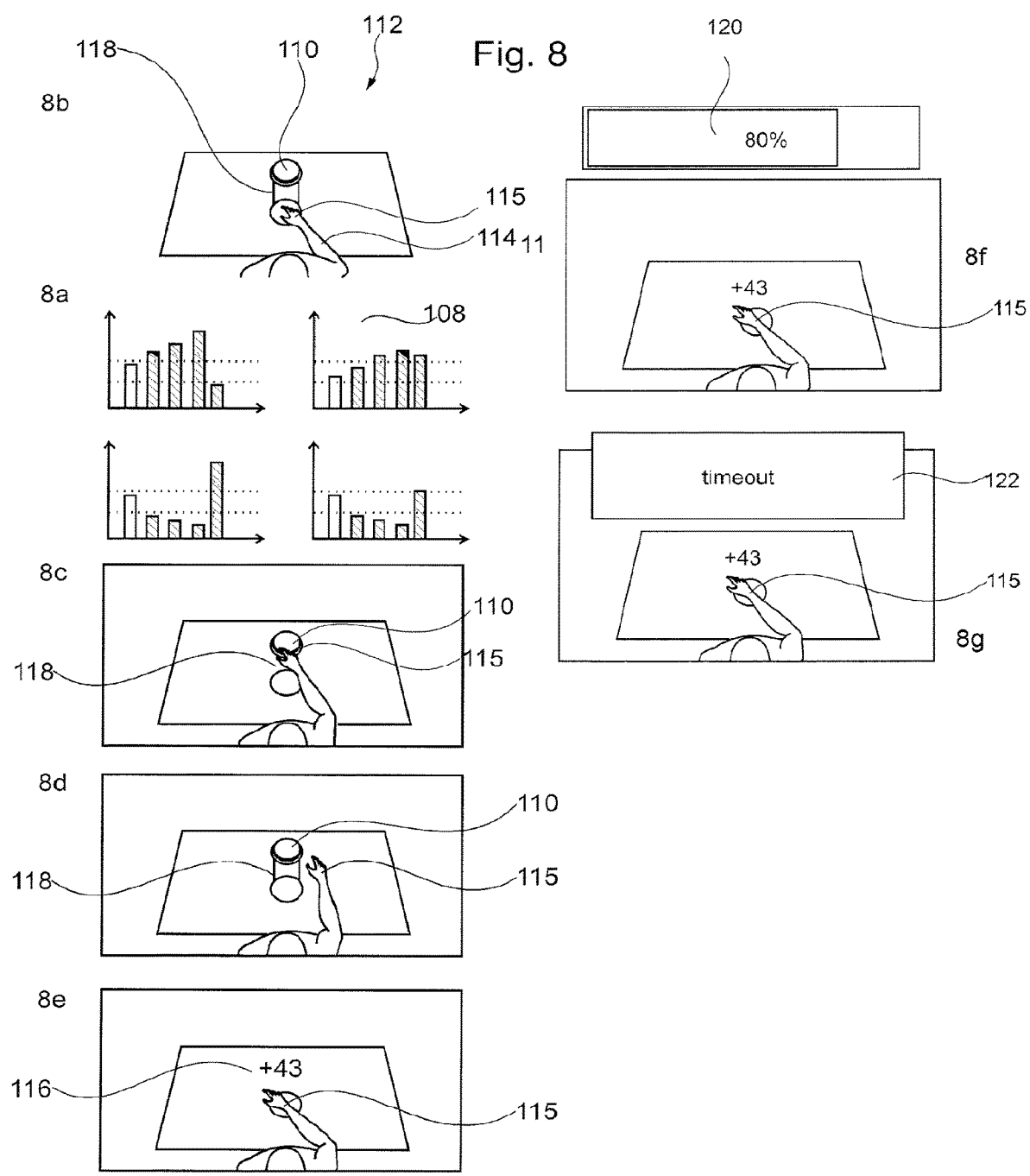
FIG. 8 is a view of screen shots which are displayed to a user during the process of FIG. 7.

FIGS. 7 and 8a-8g describe the process in more detail. At stage 1 in FIG. 7, a user, such as a patient or operator, interfaces with a user input of the exercise logic unit 84 of the VR generation module 58 to select a task from a library of tasks which may be stored. In this example a 'reach an object task' is selected. At this stage the user may be provided with the results 108 of previous like tasks, as shown in FIG. 8a. These results may be provided to aid in the selection of the particular task or task difficulty. The user may also input parameters to adjust the difficulty of the task, for example based on a level of success from the previous task.

At stage 2, the exercise logic unit 84 initializes the task. This comprises steps of the exercise logic unit 84 interfacing with the VR environment unit 86 to retrieve the parts (such as the disk 110) associated with the selected task from a library of parts. The exercise logic unit 84 also interfaces with the body model unit 88 to retrieve, from a library of body parts, a 3D point cloud model of the body part (in this example a single arm 114) associated with the exercise. The body part data is then supplied to the avatar posture generation unit 90 so that an avatar of the body part 114 can be created. The VR content integration unit 92 receives data in relation to the avatar of the body part and parts in the VR environment and integrates them in a VR environment. This data is thereafter received by the exercise logic unit 84 and is output to the display means 34 of the head set 2 as shown in FIG. 8b. The target path 118 for the user to move a hand 115 of the arm 114 along is indicated, for example, by colouring it blue.

At stage 3, the exercise logic unit 84 interrogates the skeletal tracking module 16 to determine whether any arm movement has occurred. The arm movement being derived from the sensors of the position/motion detection system 16 which are worn by the user. If a negligible amount of movement (for example an amount less than a predetermined amount, which may be determined by the state of the user and location of movement) or no movement has occurred then stage 5 is executed, else stage 4 is executed.

At stage 4 the exercise logic unit 84 processes the movement data to determine whether the movement is correct. If the user has moved their hand 115 in the correct direction, for example, towards the object 110, along the target path 118, then stage 4a is executed and the colour of the target path may change, for example it is coloured green, as shown in FIG. 8c. Else, if the user moves their hand 115 in an incorrect direction, for example, away from the object 110, Then stage 4b is executed and the colour of the target path may change, for example it is coloured red, as shown as FIG. 8d.

Following stage 4a and 4b stage 4c is executed, wherein the exercise logic unit 84 determines whether the hand 115 has reached the object 110. If the hand has reached the object, as shown in FIG. 8e then stage 6 is executed, else stage 3 is re-executed.

At stage 5 the exercise logic unit 84 interrogates the physiological parameter processing module 52 to determine whether any physiological activity has occurred. The physiological activity is derived from the sensors of the physiological parameter sensing system module 14, which are worn by the user, for example the EEG and/or EMG sensors. EEG and EMG sensors may be combined to improve detection rates, and in the absence of a signal from one type of sensor a signal from the other type of sensor maybe used. If there is such activity, then it may be processed by the exercise logic unit 84 and correlated to a movement of the hand 115. For example a characteristic of the event related data segment from the physiological parameter processing module 52, such as the intensity or duration of part of the signal, may be used to calculate a magnitude of the hand movement 115. Thereafter stage 6 is executed.

At stage 5a if the user has successfully completed the task, then to provide feedback 116 to the user a reward score may be calculated, which may be based on the accuracy of the calculated trajectory of the hand 115 movement. FIG. 8e shows the feedback 116 displayed to the user. The results from the previous task may also be updated.

Thereafter stage 6b is executed, wherein a marker strength of the sensors of the physiological parameter sensing system module 14, for example the EEG and EMG, sensors may be used to provide feedback 118. FIG. 8f shows an example of the feedback 120 displayed to the user, wherein the marker strength is displayed as a percentage of a maximum value. The results from the previous task may also be updated. Thereafter, stage 7 is executed, wherein the task is terminated.

As stage 8 if there is no data provided by either of the sensors of the physiological parameter sensing system module 14 or the sensors of the position/motion detection system 16 with in a set period of time then time out 122 occurs, as shown in FIG. 8g and stage 7 is executed.

EXAMPLE 2

Hybrid Brain-Computer Interface with Virtual Reality Feedback with Head-Mounted Display, Robotic System and Functional Electrical Stimulation Objective: To provide optimal training for patients with upper movements movement deficits resulting from neurological problems (e.g., ALS, stroke, brain injury, locked-in syndrome, Parkinson disease etc.). These patients would require training to reintegrate the lost/degraded movement function. A system that reads their intention to make a functional movement and provide an assistance in completing the movement could enhance the rehabilitation outcome.

For this purpose, the system could exploit Hebbian learning in associating brain's input and output areas in reintegrating the lost movement function. The Hebbian principle is "Any two systems of cells in the brain that are repeatedly active at the same time will tend to become 'associated', so that activity in one facilitates activity in the other."

In the present example, the two systems of cells are the areas of the brain that are involved in sensory processing and in generating motor command. When the association is lost due to neural injury, it could be restored or re-built via Hebbian training. For the optimal results of this training, one must ensure near perfect synchronization of system inputs and outputs and in providing realtime multi-sensory feedback to the patient with small delay and more importantly almost negligible jitter.

Figure 9:
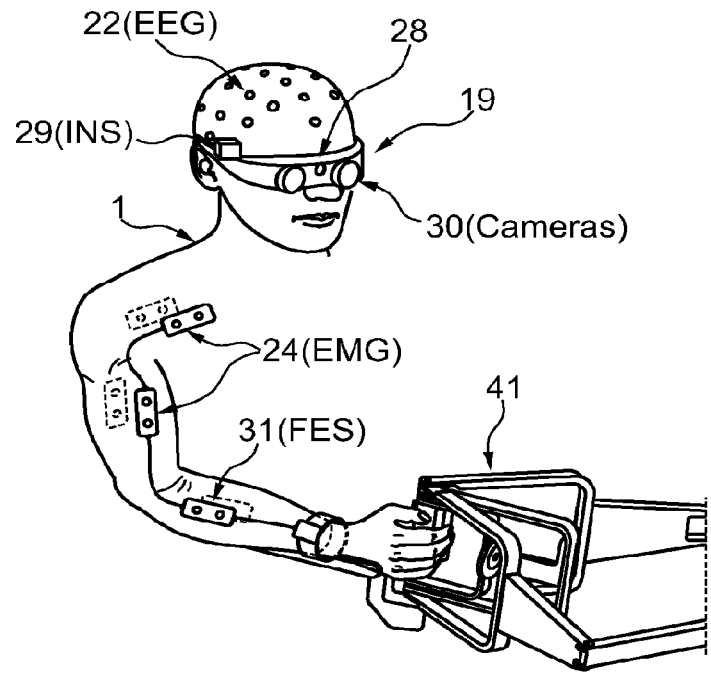
FIG. 9 is a perspective view of a physical setup of a physiological parameter measurement system according to an exemplary embodiment of the invention.

The physical embodiment illustrated in FIG. 9, comprises a wearable system having a head-mounted display (HMD) 19 to display virtual reality 3D video content on microdisplays (e.g., in first person perspective), a stereo video camera 30 and a depth camera 28, whose data is used for tracking the wearer's own arm, objects and any second person under the field of view (motion tracking unit).

Additionally, the EEG electrodes 22 placed over the head of the wearer 1, integrated in a head set 2 as previously described (not shown in detail in this figure for simplification), EMG electrodes 24 placed on the arm will measure electrical activity of the brain and of muscles respectively, used for inferring users intention in making a goal directed movement. Additionally, there exists an Inertial Measurement Unit (IMU) 29 that is used for tracking head movements. The executed or intended movements are rendered in the virtual reality display. In case of evidence of the movements through the biological sensor data (ie, EEG, EMG, and motion tracing) feedback mechanisms aid the patient in making goal directed movement using a robotic system 41. Furthermore, functional electrical stimulation (FES) system 31 activates muscles of the arm in completing the planned movement. Additionally, the feedback mechanisms shall provide appropriate stimulation tightly coupling to the intention to move to ensure the implementation of Hebbian learning mechanism.

Figure 10:
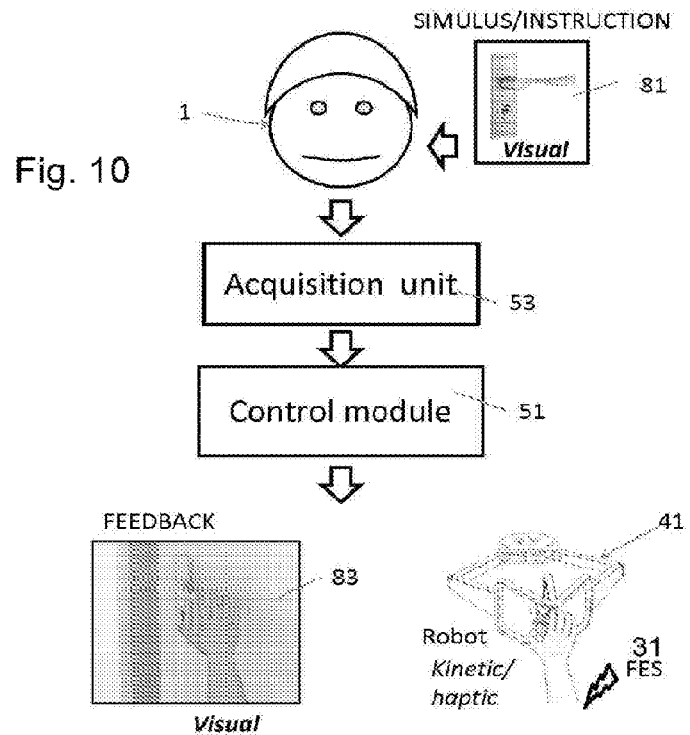
FIG. 10 is a schematic block diagram of an example stimulus and feedback trial of a physiological parameter measurement system according to an exemplary embodiment of the invention.

The following paragraph describes a typical trial in performing a typical goal directed task, which could be repeated by the patient several times to complete a typical training session. As shown in FIG. 10, a 3D visual cue 81, in this case a door knob, when displayed in the HMD could instruct the patient 1 to make a movement corresponding to opening the door. Followed by the visual cue, the patient may attempt to make the suggested movement. Sensor data (EEG, EMG, IMU, motion data) is acquired in synchronization with the moment of presentation of the visual cue. The control system 51 then extracts the sensor data and infers user intention and a consensus is made in providing feedback to the user through a robot 41 that moves the arm, and HMD displays movement of an avatar 83, which is animated based on the inferred data. A Functional Electrical Stimulation (FES) 31 is also synchronized together with other feedbacks ensuring a congruence among them.

Figure 2D:
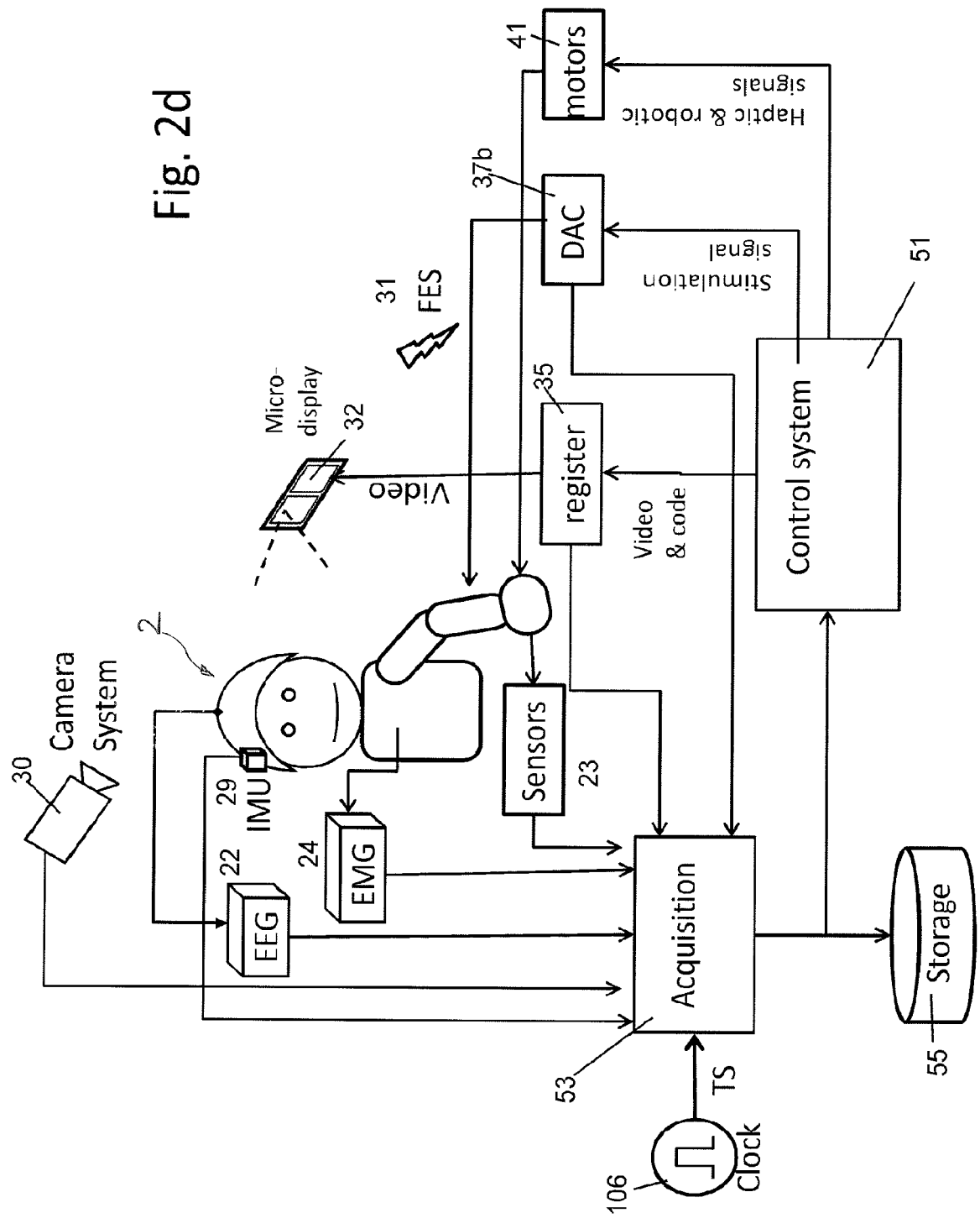
FIG. 2d is a schematic diagram illustrating an embodiment of the invention in which a haptic feedback system is included.

An exemplary architecture of this system is illustrated in FIG. 2d. The acquisition unit acquires physiological data (i.e., EEG 22, EMG 24, IMU 29 and camera system 30). The camera system data include stereo video frames and depth sensor data. Additionally the stimulation related data such as the moment at which a particular image frame of the video is displayed on the HMD, robot's motor data and sensors 23 and that of FES 31 stimulation data are also sampled by the acquisition unit 53. This unit associates each sensor and stimulation sample with a time stamp (TS) obtained from the clock input. The synchronized data is then processed by control system and is used in generating appropriate feedback content to the user through VR HMD display, robotic movement as well as FES stimulation.

Inputs of the System:
  Inertial measurement unit (IMU) sensors 29, for instance including an accelerometer, a gyroscope, a magnetometer: Purpose, to track head movements. This data is used for rendering VR content as well as to segment EEG data where the data quality might be degraded due to movement.
  Camera system 30, 28: The camera system comprises a stereo camera 30, and a depth sensor 28. The data of these two sensors are combined to compute tracking data of a wearer's own movements of upper limbs, and for tracking wearer's own arm movements. These movements are then used in animating the avatar in the virtual reality on micro displays 32 and in detecting if there was a goal directed movements, which is then used for triggering feedback through display 32, robot 41, and stimulation device FES 31. In an exemplary application of the invention the sensors EEG 22 & EMG 24 may be used for inferring if there was an intention to make a goal directed movement.

Outputs of the System/Feedback Systems
  Micro-displays 34 of head set 2: Renders 2D/3D virtual reality content, where a wearer experiences the first person perspective of the virtual world as well as of his own avatar with its arms moving in relation to his own movements.
  Robotic system 41: Robotic system described in this invention is used for driving movements of the arm, where the user 1 holds a haptic knob. The system provides a range of movements as well as haptic feedback of natural movements of activities of daily living.
  Functional Electrical Stimulation (FES) device 31: Adhesive electrodes of FES system are placed on user's arms to stimulate nerves, which up on activated can restore the lost voluntary movements of the arm. Additionally, the resulting movements of the hand results in kinesthetic feedback to the brain.

Data Processing
  The following paragraphs describe the data manipulations from inputs till outputs.

Figure 11:
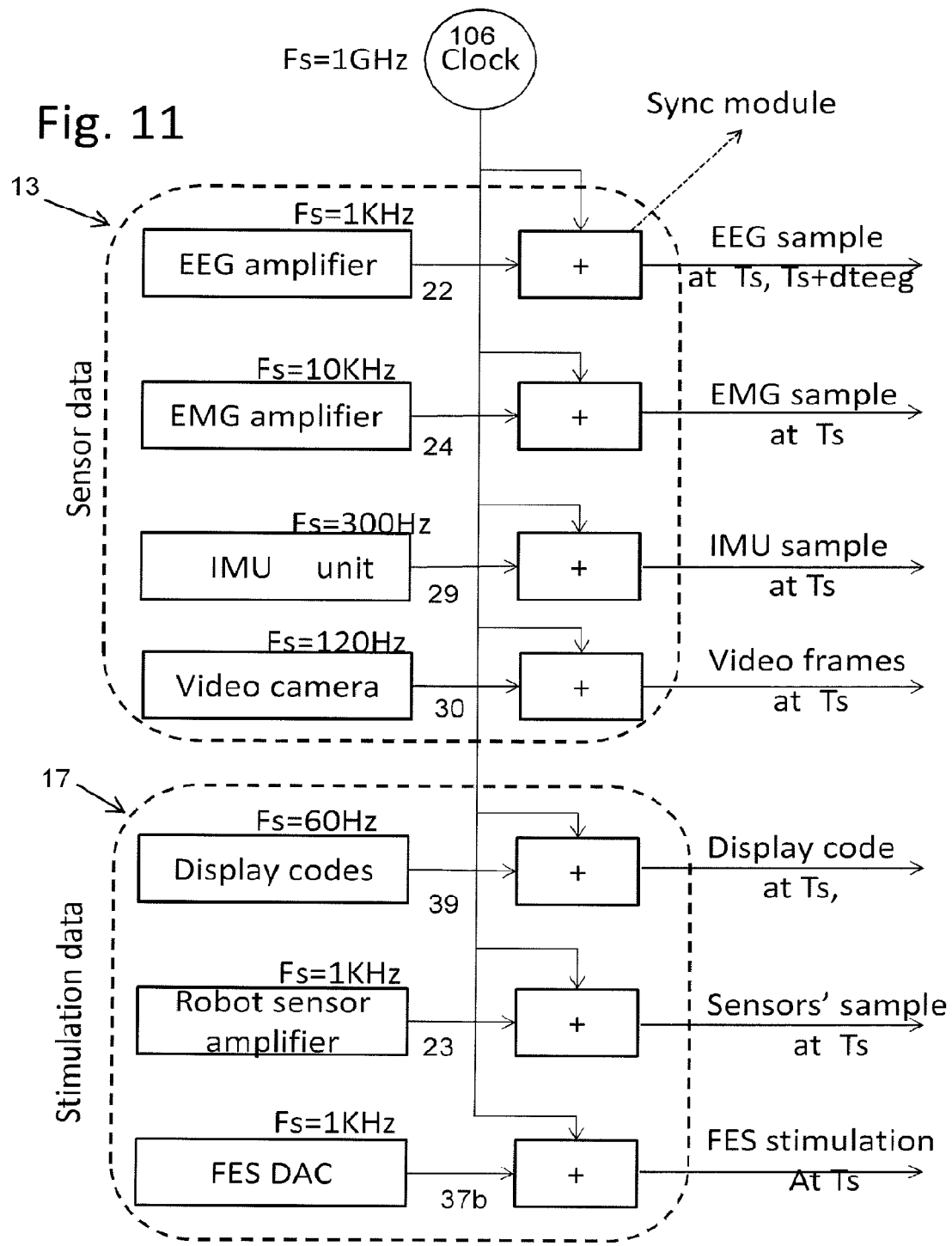
FIG. 11 is a schematic block diagram of an acquisition module of a physiological parameter measurement system according to an exemplary embodiment of the invention.

Acquisition Unit 53:
  The description of acquisition unit 53 ensures near perfect synchronization of inputs/sensor data and outputs/Stimulation/feedback of the system as illustrated in the FIG. 11. Each sensor data may have different sampling frequency and whose sampling may have not initiated at exact same moment due to non-shared internal clock. In this example, the sampling frequency of EEG data is 1 kHz, EMG data is 10 KHz, IMU data is 300 Hz. Video camera data is 120 frames per second (fps). Similarly, the stimulation signals have different frequencies, where the display refresh rate is at 60 Hz, robot sensors of 1 KHz, and FES data at 1 KHz.

The acquisition unit 53 aims at solving the issue of synchronization of inputs and outputs accurately. In achieving so, the outputs of the system are sensed either with dedicated sensors or indirectly recorded from a stage before stimulation, for instance as follows:
  Sensing the micro-display: Generally, the video content that is generated in the control system is first pushed to a display register 35 (a final stage before the video content is activated on the display). Together with video content, the controller sends a code to a part of the register (say N bits) corresponding to one or more pixels (not too many pixels, so that the user is not disturbed). The corner pixels in the micro display are preferred as they may not be visible to user. The codes (a total of 2^N) may be defined by the controller or the exercise logic unit describing the display content.
  Sensing FES: The FES data can be red from its last stage of generation, i.e., from the DAC.
  Sensing Robot's movements: The robots motors are embedded with sensors providing information on angular displacement, torque and other control parameters of the motors.

Figure 12:
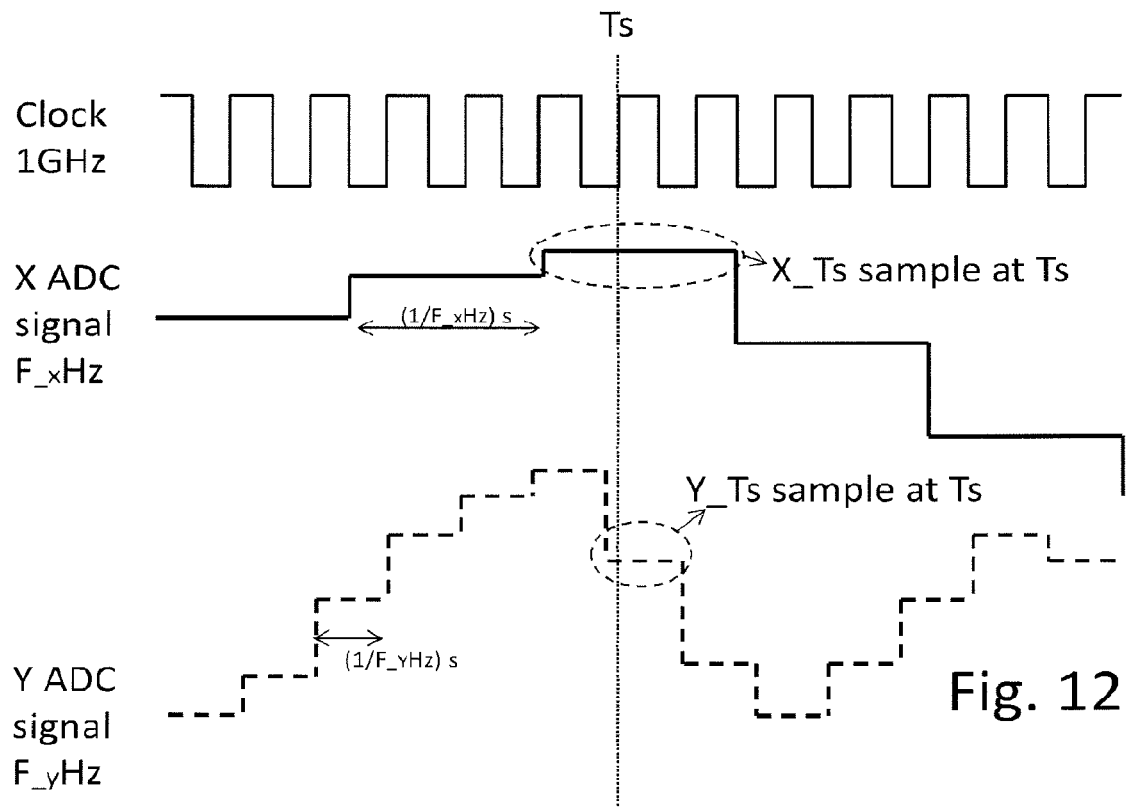
FIG. 12 is a diagram illustrating time stamping of a signal by a clock module of a physiological parameter measurement system according to an exemplary embodiment of the invention.

Now using a clock signal with preferably a much higher frequency than that of the inputs and outputs (e.g., 1 GHz), but at least double the highest sampling frequency among sensors and stimulation units, the acquisition module reads the sensor samples and attaches a time stamp as illustrated in the FIG. 12. When a sample of a sensor arrives from its ADC 37a, its time of arrival is annotated with next immediate rising edge of the clock signal. Similarly for every sensor and stimulation data a time-stamp is associated.

When these samples arrive at the controller, it interprets the samples according to the time stamp of arrival leading to minimized jitters across sensors and stimulations.

Physiological Data Analysis

The physiological data signals EEG and EMG are noisy electrical signals and preferably are pre-processed using appropriate statistical methods. Additionally the noise can also be reduced by better synchronizing the events of stimulation and behavior with the physiological data measurements with negligible jitter.

Figure 13:
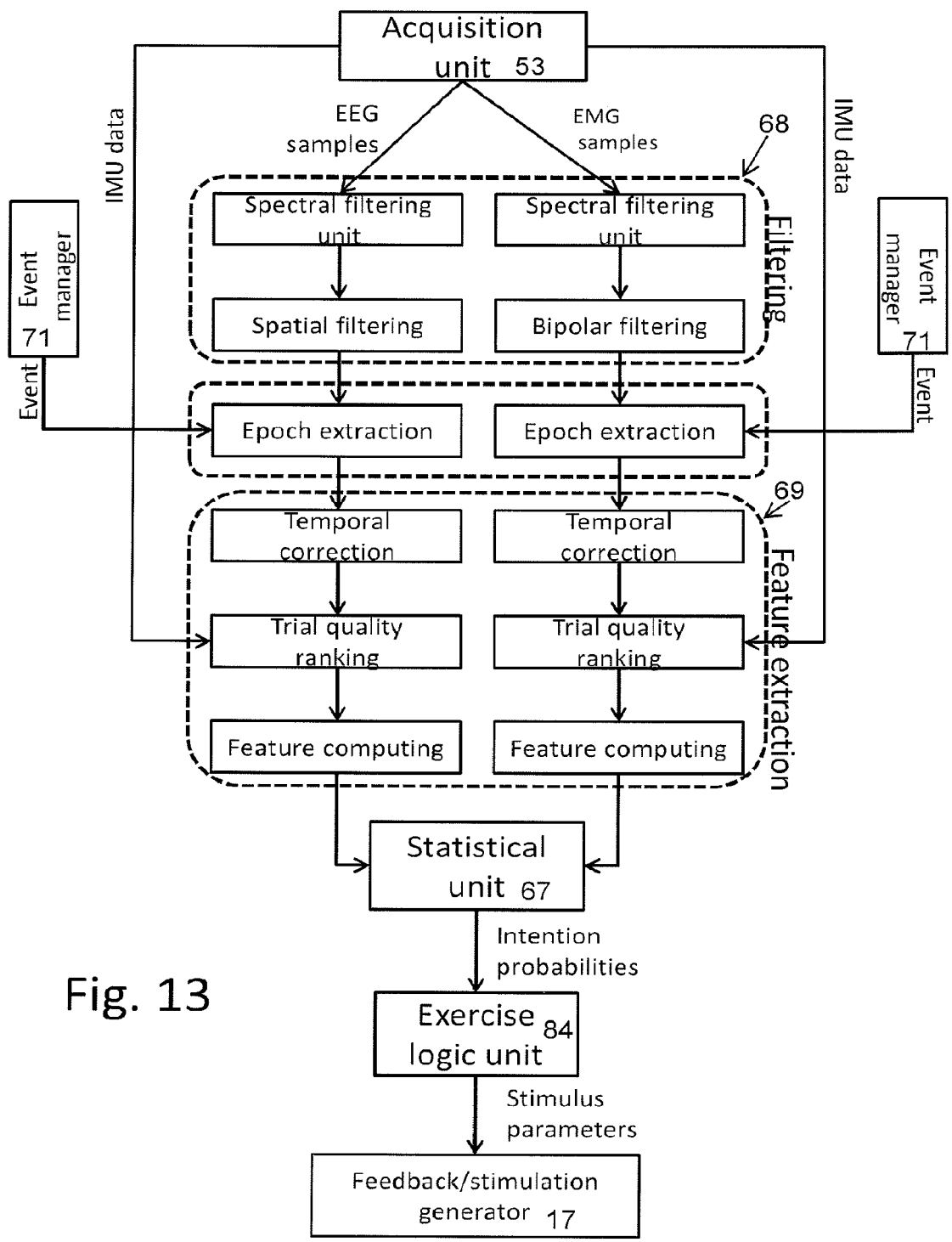
FIG. 13 is a data-flow diagram illustrating a method of processing physiological signal data in a control system of a physiological parameter measurement system according to an exemplary embodiment of the invention.

FIG. 13 illustrates various stages of the pre-processing (filtering 68, epoch extraction and feature extraction stages). EEG samples from all the electrodes are first spectrally filtered in various bands (e.g., 0.1-1 Hz, for slow cortical potentials, 8-12 Hz for alpha waves and Rolandic mu rhythms, 18-30 Hz for beta band and from 30-100 Hz for gamma band). Each of these spectral bands contains different aspects of neural oscillations at different locations. Following this stage the signals undergo spatial filtering to improve signal-to-noise ratio additionally. The spatial filters include simple processes such as common average removal to spatial convolution with Gaussian window or Laplace windows. Following this stage the incoming samples are segmented into temporal windows based on event markers arriving from event manager 71. These events correspond to the moment the patient is given a stimulus or made a response.

These EEG segments are then fed to feature extraction unit 69, where temporal correction is first made. One simple example of temporal correction is removal of baseline or offset from the trial data from a selected spectral band data. The quality of these trials may be assessed using statistical methods such as Outlier's detection. Additionally, if there is a head movement registered through IMU sensor data, the trials are annotated as artefact trials. Finally features are computed from each trial that well describe the underlying neural processing. These features are then fed to a statistical unit 67.

Similarly, the EMG electrode samples are first spectrally filtered, and applied a spatial filter. The movement information is obtained from the envelope or power of the EMG signals. Similar to EEG trials, EMG spectral data is segmented and passed to feature extraction unit 69. The output of EMG feature data is then sent to statistical unit 67.

The statistical unit 67 combines various physiological signals and motion data to interpret the intention of the user in performing a goal directed movement. This program unit includes mainly machine learning methods for detection, classification and regression analysis in interpretation of the features. The outputs of this module are intention probabilities and related parameters which drive the logic of the exercise in the Exercise logic unit 84. This exercise logic unit 84 generates stimulation parameters which are then sent to a feedback/stimulation generation unit of the stimulation system 17.

Throughout these stages, it is ensured to have minimal lag and more importantly least jitter.

Event Detection & Event Manager

Figure 14:
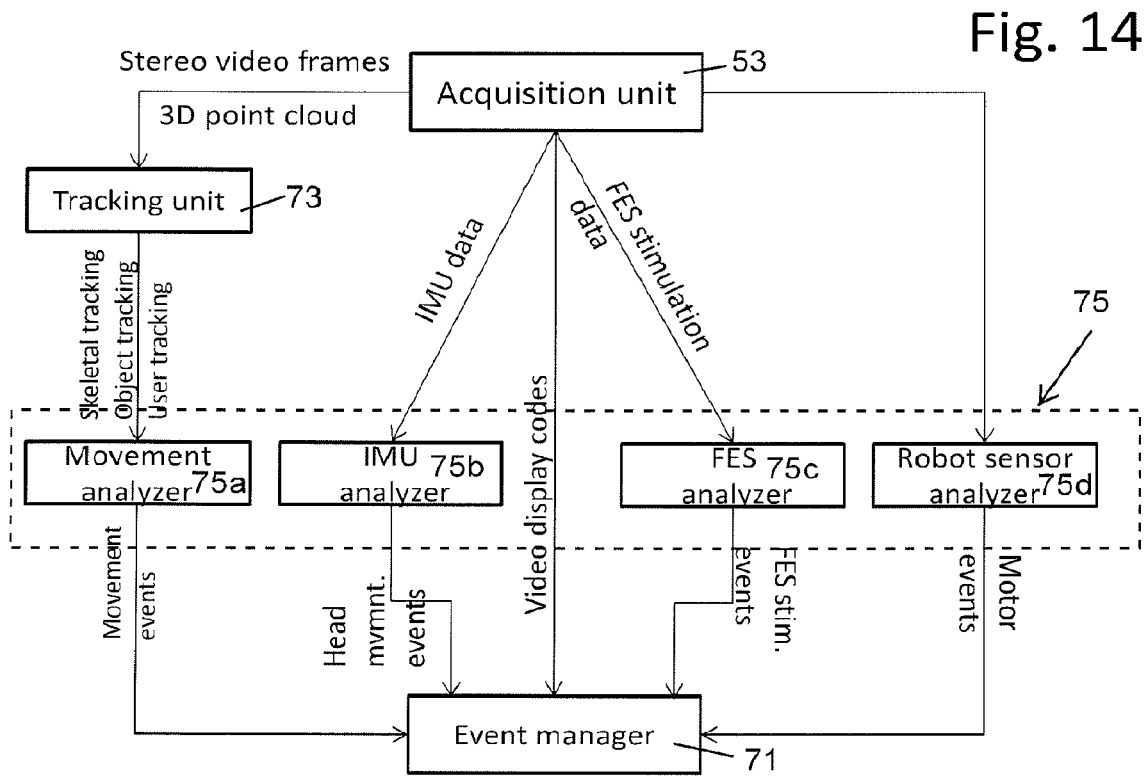
FIG. 14 is a flowchart diagram illustrating a method of processing events in a control system of a physiological parameter measurement system according to an exemplary embodiment of the invention.

Events such as the moment at which the patient is stimulated or presented an instruction in the VR display, the moment at which the patient performed an action are necessary for the interpretation of the physiological data. FIG. 14 illustrates event detection. The events corresponding to movements and those of external objects or of a second person need to be detected. For this purpose the data from camera system 30 (stereo cameras, and 3D point cloud from the depth sensor) are integrated in the tracking unit module 73 to produce various tracking information such as: (i) patient's skeletal tracking data, (ii) object tracking data, and (iii) a second user tracking data. Based on the requirements of the behavioral analysis, these tracking data may be used for generating various events (e.g., the moment at which patient lifts his hand to hold door knob).

IMU data provides head movement information. This data is analyzed to get events such as user moving head to look at the virtual door knob.

The video display codes correspond to the video content (e.g., display of virtual door knob, or any visual stimulation). These codes also represent visual events. Similarly FES stimulation events, Robot movement and haptic feedback events are detected and transferred into event manager 71. Analyzer modules 75, including a movement analyzer 75a, an IMU analyzer 75b, an FES analyzer 75c and a robot sensor analyzer 75d, process the various sensor and stimulation signals for the event manager 71.

The event manager 71 then sends these events for tagging the physiological data, motion tracking data etc. Additionally these events also sent to Exercise logic unit for adapting the dynamics of exercise or challenges for the patient.

Other Aspects of Control System

The control system interprets the incoming motion data, intention probabilities from the physiological data and activates exercise logic unit and generates stimulation/feedback parameters. The following blocks are main parts of the control system.

VR feedback: The motion data (skeletal tracking, object tracking and user tracking data) is used for rendering 3D VR feedback on the head-mounted displays, in form of avatars and virtual objects.

Exercise logic unit 84: The exercise logic unit implements sequence of visual display frames including instructions and challenges (target task to perform, in various difficulty levels) to the patient. The logic unit also reacts to the events of the event manager 71. Finally this unit sends stimulation parameters to the stimulation unit.

Robot & FES stimulation generation unit: this unit generates inputs required to perform a targeted movement of the robotic system 41 and associated haptic feedback. Additionally, stimulation patterns (current intensity and electrode locations) for the FES module could be made synchronous and congruent to the patient.

EXAMPLE 3

Brain Computer Interface and Motion Data Activated Neural Stimulation with Augmented Reality Feedback Objective A system could provide precise neural stimulation in relation to the actions performed by a patient in real world, resulting in reinforcement of neural patterns for intended behaviors.

Description

Actions of the user and that of a second person and objects in the scene are captured with a camera system for behavioral analysis. Additionally neural data is recorded with one of of the modalities (EEG, ECOG etc.) are synchronized with IMU data. The video captured from the camera system is interleaved with virtual objects to generate 3D augmented reality feedback and provided to the user though head-mounted display. Finally, appropriate neural stimulation parameters are generated in the control system and sent to the neural stimulation.

For delay and jitter between users behavioral and physiological measures and neural stimulation should be optimized for effective reinforcement of the neural patterns.

Figure 2E:
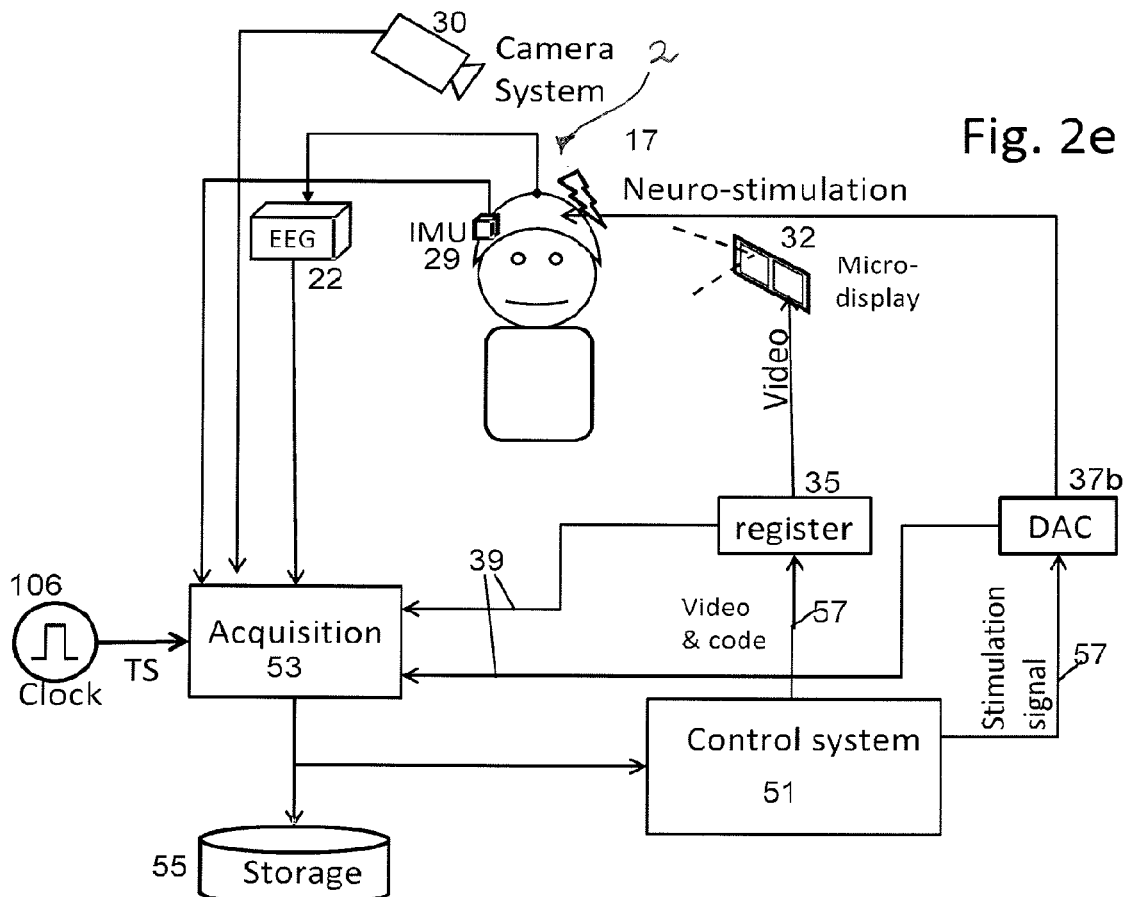
FIG. 2e is a schematic diagram illustrating an embodiment of the invention in which a neuro-stimulation signal is applied to a user.

The implementation of this example is similar to Example 2, except that the head-mounted display (HMD) displays Augmented Reality content instead of Virtual Reality (see FIG. 2e). Meaning, virtual objects are embedded in 3D seen captured using stereo camera and displayed on micro displays insuring first person perspective of the scene. Additionally, direct neural stimulation in implemented through such as deep brain stimulation and cortical stimulation, and non-invasive stimulations such as trans-cranial direct current stimulation (tDCS), trans-cranial alternating current stimulation (tACS), trans-cranial magnetic stimulation (TMS) and trans-cranial Ultrasonic stimulation. The system can advantageously use one or more than one stimulation modalities at time to optimize the effect. This system exploits the acquisition unit described in the example 1.

List of References

10 Physiological parameter measurement and motion tracking system
2 Head set
   3 EEG sensing device
      4 EEG sensor support
         4a central branch
         4b front lateral branch
            4b1, 4b2 back and side extensions
         4c center lateral branch
            4c1, 4c2 front, rear extensions
         4d rear lateral branch
            4d1, 4d2 front and side extensions
         401 base wall
            404 electrode orifices
                404a electrode orifice portion
                404b through passage portion
            405 tensioner anchors→fixing orifices
            406 bottom surface
         402 side walls
         403 channel
      5 potting material (top wall)
         top surface 506
      6 Flexible circuit
         22 EEG sensors
            221 EEG electrodes
      8 EEG signal processing circuit
         8a discrete EEG signal amplifiers
         8b circuit traces
         601 flexible circuit substrate
            602 electrode orifice
            605 tensioner orifice
         6a central branch
         6b front lateral branch
            6b1, 6b2 back and side extensions
         6c center lateral branch
            6c1, 6c2 front, rear extensions
         6d rear lateral branch
            6d1, 6d2 front and side extensions
         41 connection portion
   7 tensioners→elastic ties
   37 conducting gel
   9 head mount frame support
      strap
      adjustment knob
19 Head-mounted display
   32 Display unit
      34 Display means
      35 Display register
   36 Display unit support
   33 Audio unit
   100 Eye gaze sensing Unit
      102 eye gaze sensor
   40 Head movement sensing Unit
      42 Movement sensing unit
         44 Acceleration sensing means
         47 Head orientation sensing means
            46 Gyroscope
            48 Magnetometer
      50 movement sensing unit support (mount to HMD system)
12 Control system
   51 Control module
      57 output signals (video, audio, stimulation)
   53 Acquisition module
   55 Memory
   52 Skeletal tracking Module
      60 Data fusion unit
      62 Calibration unit
      64 Skeletal tracking unit
   54 Physiological parameter processing Module
      66 Re-referencing unit
      68 Filtering unit
         70 Spectral filtering module
         72 Spatial smoothing filtering module
         74 Laplacian filtering module
      76 Event marking unit
      78 Artefact unit
         80 Artefact detecting module
         82 Artefact removal module
      69 feature extraction unit
      67 statistical unit
   56 Head tracking module
   104 Eye gaze tracking module
   58 VR generation module
      84 Exercise logic unit
      Input unit
      86 VR environment unit
      88 Body model unit
      90 Avatar posture generation unit
      92 VR content integration unit
      94 Audio generation unit
      96 Feedback generation unit
   106 Clock module
   71 Events manager
   73 Tracking unit
      User tracking
         →64 Skeletal tracking unit
         →104 Eye gaze tracking module
      Object tracking
   75 Analyzer modules
      75a Movement
      75b IMU
      75c FES
      75d Robot sensor 13 Sensing system
 14 Physiological parameter sensing system
  20 Sensors
   22 Electroencephalogram (EEG) sensors
   24 Electromyogram (EMG—connected to muscles in body
   25 Electrooculography (EOG)—eye movement sensor
   27 Electrocardiogram (ECG)
   29 Inertial Sensor (INS)/Inertial measurement unit (IMU) sensor
   40 Head movement sensing Unit
   Body temperature sensor
   Galvanic skin sensor
  16 Position/motion detection system
   26 Sensors
    28 Depth/distance sensor
    30 Camera (colour)
  21 sensor output signals
17 Stimulation system
 31 Functional Electrical Stimulation (FES) system
 Audio stimulation system→audio unit 33
 Video stimulation system→display unit 32
 37a Analogue to Digital Converter (ADC)
 37b Digital to Analogue Converter (DAC)
 39 content code signal
 41 Haptic feedback device→robot
  23 user feedback sensors

What is claimed is:

1. A headset comprising:
a brain electrical activity (EEG) sensing device comprising EEG sensors configured to be mounted on a head of a wearer so as to position the EEG sensors at selected positions of interest over the wearer's scalp, a sensor support and a flexible circuit assembled to the sensor support, the sensor support and the flexible circuit comprising a central stem configured to extend along a center plane of the top of the wearer's head in a direction from nasion to inion, a front lateral branch configured to extend across a front portion of the wearer's head extending laterally from the central stem, a center lateral branch configured to extend across a top portion of the wearer's head between the wearer's ears, and a rear lateral branch configured to extend across a back portion of the wearer's head, wherein the sensor support comprises a base wall having a first side to contact the head of the wearer and side walls extending along edges of an opposite side of the base wall to form an essentially flat "U" shaped channel in which the flexible circuit is inserted and the base wall comprise EEG sensor orifices to receive a gel to allow electrical contact to be established between the scalp of the wearer and contacts of EEG sensors on the flexible circuit; further comprising a head-mounted display (HMD) fixed to a head mount frame support, wherein said "U" shaped channel is configured to bend to conform to a generally spherical or ellipsoid three dimensional form corresponding essentially to the general morphology of a top half of the wearer's head; and
the head-mounted display (HMD) fixed to a head mount frame support and configured to be positioned over the eyes of the wearer of the headset, wherein the HMD comprises a display unit having a display comprising an electronic screen configured for positioning in front of the wearer's eyes to present visual information to the wearer, wherein said visual information is provided as part of a VR (virtual reality) environment or an AR (augmented reality) environment, the HMD further comprising a position/motion detection system operable to detect a position/motion of a body part of the wearer, the position/motion/detection system comprising one or more color cameras, and a depth sensor.

2. The headset according to claim 1 wherein each of the lateral branches further comprises extensions extending in a front to rear or in a rear to front direction, and wherein the EEG sensors are positioned in discrete spaced apart positions along the stem, branches and extensions.

3. The headset according to claim 1 wherein a top wall or flexible sealing material is mounted or filled over the flexible circuit in the "U" shaped channel in order to seal in a waterproof manner the electrical circuit tracks and components on the flexible circuit within the "U" shaped channel.

4. The headset according to claim 1 wherein the sensor support is a single piece part molded or formed from a flexible polymeric material.

5. The headset according to claim 1 wherein the flexible circuit comprises a single piece flexible substrate.

6. The headset according to claim 2 wherein the sensor support further comprises tensioner anchors configured to anchor elastic tensioners between positions in the stem, branches and extensions of the EEG sensing device, and also between the EEG sensing device and a head mount frame support wherein the flexible circuit comprises orifices for the tensioning anchors.

7. The headset according to claim 1 wherein next to each EEG sensor on the flexible circuit a discrete EEG signal amplifier is positioned configured to amplify the brain electrical activity signal picked up by the corresponding EEG sensor.

8. The headset according to claim 1 wherein the EEG sensors comprise electrodes in the form of conductive circuit pads on a surface of a substrate of the flexible circuit intended to face the wearer's scalp.

9. The headset according to claim 1 wherein the EEG sensors comprise protruding conductive compressible elements mounted on the flexible substrate and electrically connected to a circuit trace of a substrate of the flexible circuit.

10. The headset of claim 1, further comprising a head movement sensing unit at the HMD.

11. The headset according to claim 1 further comprising a wireless communication device to interconnect the HMD to external electronic devices and computing systems in a wireless fashion and an onboard power supply to power the HMD, located at the HMD.

12. The headset according to claim 1, wherein the headset further incorporates a plurality of sensors configured to measure different physiological parameters, selected from a group consisting of ECOG sensors, eye movement sensors, and head movement sensing unit.

13. The headset according to claim 7, wherein the flexible circuit comprises a pluggable electrical connector for plugging to a complementary pluggable electrical connector on the HMD.

14. The headset according to claim 1, wherein the flexible circuit comprises orifices adjacent the EEG sensor contacts or electrodes, and wherein the EEG sensor orifices overlap the flexible circuit orifices such that a through passage between a top surface and a bottom surface of the sensing device is provided.

15. A physiological parameter measurement system comprising a headset, a control system, a sensing system and a stimulation system, the sensing system comprising one or more physiological sensors including at least brain electrical activity sensors mounted in the headset, the EEG sensors configured to be mounted on a head of a wearer at selected positions of interest over the wearer's scalp, the headset comprising a sensor support and a flexible circuit assembled to the sensor support, the sensor support and flexible circuit comprising a central stem configured to extend along a center plane of the top of the head in a direction from nasion to inion, a front lateral branch configured to extend across a front portion of a wearer's head extending laterally from the central stem, a center lateral branch configured to extend across a top portion of a wearer's head essentially between the wearer's ears, and a rear lateral branch configured to extend across a back portion of a wearer's head, the stimulation system comprising one or more stimulation devices including at least a visual stimulation system, the control system comprising an acquisition module configured to receive sensor signals from the sensing system, and a control module configured to process the signals from the acquisition module and control the generation of stimulation signals to one or more devices of the stimulation system, wherein the control system further comprises a clock module and wherein the control system is configured to time stamp signals related to the stimulation signals and the sensor signals with a clock signal from the clock module, enabling the stimulation signals to be synchronized with the sensor signals by means of the time stamps, and wherein said time stamped signals related to the stimulation signals comprise content code signals received from the stimulation system; wherein the sensing system comprises physiological sensors selected from a group comprising Electromyogram (EMG) sensors, Electrooculography (EOG) sensors, Electrocardiogram (ECG) sensors, Inertial Sensors (INS), Body temperature sensor, Galvanic skin sensor, pulse oximetry sensor, respiration sensors; and wherein the stimulation system comprises stimulation devices selected from a group comprising audio stimulation device, Functional Electrical Stimulation (FES) devices, and haptic feedback devices, said functional electrical stimulation (FES) devices being connected to the control system and operable to electrically stimulate one or more body parts of the user, the FES devices selected from a group consisting of electrodes configured to stimulate nerves or muscles, trans-cranial alternating current stimulation (tACS), direct current stimulation (tDCS), trans-cranial magnetic stimulation (T S) and trans-cranial ultrasonic stimulation; further comprising a display register configured to receive display content representing a final stage before the display content is activated on the display, the display register being configured to generate a display content code signal for transmission to the control system, a time stamp being attached to the display content code signal by the clock module.

16. The system according to claim 15 wherein each stimulation device comprises with an embedded sensor whose signal is registered by a synchronization device.

17. The system according to claim 15 further comprising a robotic system for driving movements of a limb of the user and configured to provide haptic feedback.

18. The system according to claim 15 wherein the clock module is configured to be synchronized with clock module of other systems, including external computers.

19. The system according to claim 15 further comprising: an exercise logic unit configured to generate visual display frames including instructions and challenges to the display unit; and/or an events manager unit configured to generate and transmit stimulation parameters to the stimulation unit.

20. A headset comprising a brain electrical activity (EEG) sensing device comprising EEG sensors configured to be mounted on a head of a wearer so as to position the EEG sensors at selected positions of interest over the wearer's scalp, the EEG sensing device comprising a sensor support and a flexible circuit assembled to the sensor support, wherein said flexible circuit and support are configured to conform to a generally spherical or ellipsoid three dimensional form corresponding essentially to the general morphology of a top half of a human head, the sensor support and flexible circuit comprising a central stem configured to extend along a center plane of the top of the head in a direction from nasion to inion, a front lateral branch configured to extend across a front portion of a wearer's head extending laterally from the central stem, a center lateral branch configured to extend across a top portion of a wearer's head essentially between the wearer's ears, and a rear lateral branch configured to extend across a back portion of a wearer's head, characterized in that the sensor support comprises a base wall having a first side to contact the head of the wearer and side walls extending along edges of an opposite side of the base wall to form an essentially flat "U" shaped channel in which the flexible circuit is inserted and the base wall comprises EEG sensor orifices to receive a gel to allow electrical contact to be established between the scalp of the wearer and contacts of EEG sensors on the flexible circuit;

further comprising a head-mounted display (HMD) fixed to a head mount frame support and configured to be positioned over the eyes of a wearer of the headset, wherein the HMD comprises a display unit having a display comprising an electronic screen configured for positioning in front of the wearer's eyes to present visual information to the wearer, wherein said visual information is provided as part of a VR (virtual reality) environment or an AR (augmented reality) environment, the HMD further comprising a position/motion detection system operable to detect a position/motion of a body part of a user, the position/motion/detection system comprising one or more color cameras, and a depth sensor.

* * * * *